(12) United States Patent
Al Rashid et al.

(10) Patent No.: US 6,245,516 B1
(45) Date of Patent: Jun. 12, 2001

(54) DNA PROBES FOR CAMPYLOBACTER, ARCOBACTER AND HELICOBACTER

(76) Inventors: Shahnaz Tahihra Al Rashid, 36 Highland Hill, North York, Ontario (CA), M6A 2R1; Voon Loong Chan, 93 Elm Ridge Drive, Toronto, Ontario (CA), M6B 1A6

( * ) Notice: Subject to any disclaimer, the term of this patent is extended or adjusted under 35 U.S.C. 154(b) by 0 days.

(21) Appl. No.: 09/402,445

(22) PCT Filed: Apr. 8, 1998

(86) PCT No.: PCT/CA98/00333

§ 371 Date: Dec. 7, 1999

§ 102(e) Date: Dec. 7, 1999

(87) PCT Pub. No.: WO98/45473

PCT Pub. Date: Oct. 15, 1998

Related U.S. Application Data

(60) Provisional application No. 60/043,415, filed on Apr. 8, 1997.

(51) Int. Cl.[7] .............. C12Q 1/68; C12P 19/34; C07H 21/02; C07H 21/06; C12N 15/00

(52) U.S. Cl. ............. 435/6; 435/91.2; 536/23.1; 536/24.3; 935/76; 935/77; 935/78

(58) Field of Search ............ 435/6, 91.2; 536/23.1, 536/24.3; 935/76, 77, 78

(56) References Cited

PUBLICATIONS

Bourke, B. et al., *Gene* 183:219–224, 1996.
Chan, V.L. and Bingham, H. *Gene* 101:51–58, 1991.
Costas, M., et al., *Syst. Appl. Microbiol.* 9:125–131, 1987.
Elharrif, Z. and Megraud, F., *Curr. Microbiol.* 13:317–322, 1986.
Eyers, M., et al., *J. Clin. Microbiol.* 31:3340–3343, 1993.
Giesendorf, B.A., et al., *J. Clin. Microbiol.* 31:1541–1546. 1993
Giesendorf, B.A., et al., *J. Med. Microbiol.* 40:141–147, 1994.
Goodwin, C.S., et al., *J. Med. Microbiol.* 19:257–267, 1985.
Hebert, G.A., et al., *J. Clin. Microbiol.* 17:529–538, 1983.
Landegren, U. et al., *Science* 242:229–237, 1988.
Li, C., et al., *J. Clin. Microbiol.* 31:2157–2162, 1993.
Paster, B.J., et al., *Int. J. Syst. Bacteriol.* 41:31–38, 1991.
Patton, C.M., et al., *J. Clin. Microbiol.* 29:680–688, 1991.
Penner, J.L., *Clin. Microbiol. Rev.* 1:157–172, 1988.
Plamann, M., et al., *Nucleic Acids Res.* 11:2065–2075, 1983.
Totten, P.A., et al., *J. Clin. Microbiol.* 25:1747–1752, 1987.
Vandamme, P. and De Ley, J., *Int. J. Syst. Bacteriol.* 41:451–455, 1991.
Vandamme, P. et al., *Int. J. Syst. Bacteriol.* 41:88–103, 1991.
Vandamme, P. et al., *J. Clin. Microbiol.* 31:3317–3319, 1993.
Vandamme, P., et al., *Int. J. Syst. Bacteriol.* 42:344–356, 1992.
Wetherall, B.L. and Johnson, A.M. Gene Probes for Bacteria—1990. Academic Press, Inc. pp. 255–293, 1990.
Engstrand et al., J. of Clinical Microbiology 30 (9) :2295–2301 (1992).*
Wesley et al., J. of Clinical Microbiology 33 (7) : 1691–1698 (1995).*
Stanley et al., J. of General Microbiology 139 : 2495–2504 (1993).*
Stratagene Catalog p.39 (1988).*
Product insert for the GeneAmp DNA Amplification Reagent Kit from Perkin–Elmer Cetus pp. 1–2 (1988).*

* cited by examiner

*Primary Examiner*—Ethan Whisenaut
(74) *Attorney, Agent, or Firm*—Bereskin & Parr; Micheline Gravelle

(57) ABSTRACT

Nucleic acid probes and a method for their use in detecting and identifying Campylobacter, Helicobacter, and Arcobacter spp. bacterial pathogens are described. A method for prepg. specific nucleic acid probes for the detection of identification of any other bacterial pathogens is also provided.

25 Claims, 13 Drawing Sheets

FIGURE 1A

|  | S1 primer |
|---|---|
| C. jejuni | AACAAATATGCTGAAGGTTATCCGGGTAAAAGATATTATGGTGGTTGTGA |
| C. coli | AATAAATATGCTGAAGGTTATCCAGGTAAGAGATATTATGGAGGCTGTGA |
| C. lari | AATAAATATGCTGAAGGTTATCCTGGTAAAAGATATTATGGCGGATGTGA |
| C. upsaliensis | AATAAATATGCTGAAGGTTATCCGGGGAAAAGATATTATGGTGGCTGTGA |
| A. nitrofigilis | AATAAATATGCTGAAGGTTATCCATATAAAAGATATTATGGAGGGTGTGA |
| H. cinaedi | AATAACTACGCTGAAGGTTATCCAAATAAGCGGTATTATGGCGGTTGCGA |
| H. pylori | AATAAATATGCTGAAGGTTATCCTAACAAACGCTACTATGGGGGCTGTGA |

|  |  |
|---|---|
|  | ATTTGTTGATGAGATTGAAACTCTAGCTATTGAAAGATGTAAAAAACTTT |
|  | ATTTGTAGATGAAATCGAAAATTTAGCTATAGAAAGATGTAAAAAACTTT |
|  | ATTTGTAGATGAGATTGAAACGATTGCTATAGAAAGATGCAAAAAACTTT |
|  | GATTGTTGATGAAATTGAAACTCTTGCTATCCAAAGATGCAAAAAACTCT |
| AN-1 | ATTTGCTGATAAAGCAGAACAATTAGCAATAGATAGAGCTTGTGAAATTT |
| HC-1 | GTTTGTAGATAAAATCGAATCACTTGCTATTGAGCGCGTGAAGCAGCTAT |
| HP-1 | AGTGGTGGATAAAATAGAAAGCCTAGCTATAGAAAGGGCTAAAAAGCTTT |

TTAATTGTAAATTTGCTAATGTTCAGCCTAATTCAGGTTCTCAAGCTAAT
TTAATTGTAGTTTTGCAAATGTGCAACCTAATTCAGGTTCTCAAGCTAAT
TTAATTGTAATTTTGCTAATGTGCAACCTAATTCAGGCTCGCAAGCAAAT
TTAATTGTGCCTTTGCTAATGTCCAGCCAAATTCAGGCTCACAAGCAAAT
TTGGTTGTAAATTTGCAAATGTACAACCTCATGCAGGTAGTCAAGCAAAT
TTGGCTGTGCGTATGCAAATGTGCAGCCACATTCTGGCTCTCAAGCAAAT
TCAATTGCCAGTTCGCTAACGTGCAAGCGCATTCAGGCTCACAAGCCAAT

CAAGGTGTTTATGCGGCTTTGATTAATCCAGGTGATAAAATTTTAGGAAT
CAAGGCGTTTATGCTGCACTTTTAAATCCAGGTGATAAAATTTTAGGAAT
CAAGGTGTGTATATGGCATTGTTAAATCCAGGTGATAGAATTTTGGGTAT
CAAGGCGTTTATGCTGCCTTGCTTAATGCAGGAGATAGAATTTTAGGTAT
GGTGCAGTTTATGCTGCCTTAATCAATGCTGGTGATAGAATTTTAGGTAT
GGTGCGGTTTATAATGCGCTTTTAAAGCCTTATGATAAGATTCTAGGAAT
AACGCTGTCTATCACGCCCTTTTAAAGCCTTATGACAAGATTTTAGGCAT

FIGURE 1B

```
               GGATTTAAGTCATGGTGGACATTTAACTCATGGTGCAAAAGTAAGTTCTT
               GGATTTAAGTCATGGTGGACATTTAACACATGGTGCAAAAGTAAGCTCAT
               GGATTTAAGCCATGGAGGACACTTGACTCATGGTTCTAAAGTAAGTTCTT
               GGATTTAAGCCACGGAGGACATCTTACACACGGAGCTAAGGTTAGTAGCT
               GGATTTATCACATGGTGGACATTTAACTCATGGTTCTAAACCTTCATTTT
               GGATCTAAGCCATGGGCATCATCTCACACATGGCGCAAAAGTAAGTATGA
               GGATTTAAGCTGTGGAGGGCATTTAACGCATGGTGCTAAAGTGAGTTTAA

CGGGTAAAATGTACGAAAGTTGTTTTTACGGCGTAGAACTTGATGGAAGA
               CGGGAAAAATGTATGAGAGCTTTTTTTATGGTGTAGAGCTTGATGGAAGG
               CTGGAAAGGTTTATGAAAGCTTTTTTTATGGAGTTGAGCTTGATGGAAGA
               CGGGTAAAATGTATGAAAGCTTTTTTTATGGAGTTGAGCTTGATGGGCGT
               CAGGAAAAAATTATCAAGCATTTTATTATGGTGTAGAACTTGATGGTAGA
               CAGGGCAAGTGTATCAAAGCTTTTTTTATGGCGTTGGGCTTGATGGCAGG
               CCGGCAAGCATTATCAGAGCTTTTCTTATGGCGTGGGTTTGGATGGCTAT

CJATC-2        ATTGATTATGAAAAAGTAAGAGAAATTGCTAAAAAAGAAAAACCAAAAC-
CC-2           ATAAACTATGAAAAAGTTAGGGAAATTGCTCATATTGTAAAACCAAAGC-
CL-2           ATTAATTATGATAAAGTTAGAGAGATAGCAAAAGAGATTAAACCAAAAC-
CU-2           ATTAATTATGAAAAAGTAAGAGAAATAGCACACATCGTTAAGCCAAAAC-
               ATCAATTATGAGAAAGTTATGGAAATAGCAAAAGTTACTATGCCAAAAAA
               ATAGATTATAATCAAGTGCGAGAAATCGCAAAAATAGTCAAACCTC-GCC
               ATTGATTATGAAGAGACGCTAAAAATCGCTCAAAGCGTTAAGCCACAA-A
```

FIGURE 1C

```
C. jejuni       TTATAGTTTGTGGAGCTAGTGCTTATGCAAGAGTGATTGATTTTGCTAAA
C. coli         TTATCGTGTGCGGTGCGAGTGCTTATGCTCGTATTATTGACTTTTCAAAA
C. lari         TTATTGTTTGTGGTGCTAGTGCTTATCCTAGAGTGATTGATTTTGCTAAA
C. upsaliensis  TCATTGTATGCGGGGCAAGTGCTTATGCTAGGATTATTGATTTTGCTAAA
A. nitrofigilis TTATTGTTTGTGGAGCAAA-GCTGACGCAAGAGAGATTGATTTTGCTAAA
H. pylori       TTATTGTGTGTGGATTTTCAGCTTATACGCGCGAGCTTGATTTTGCGAAA
H. cinaedi      TCATTGTGTGCGGGTTTTCAGCCTATCCAAGGGAAATTGATTTTAAGAAA TTTAGAGAAATTGCTAATGAAATAGGTGCCTATCTTTTTGCTGATATAGC
                TTTAGAGAGATTGCGGATGAAGTTGGAGCTTATCTTTTTGCAGACATTGC
                TTTAGAGAAATAGCAGATGAGGTTGGTGCGTATTTGTTTGCTGATATTGC
                TTTAGAGAGATAGCCGATGAAGTGGGGCTTATCTTTTTGCAGATATTGC
                TTTAGAGAAATAGCTGATGTAGTTGGTGCAATTTTATTTGCTGATATTGC
                TTTAGAGAGATCGCAGATGAAGTGGGAGCGTTATTAATGGCTGATGTCGC
                TTTAGAGAAATCGCTGATGAAGTGGGGGCGTTACTATTAGGCGATATAGC CJATC-1         ACATATTGCAGGTCTTGTTGTGGCAGGCGAGCATCCAAGTCCTTTTCCGC
CC-1            ACACATTGCTGGACTTGTTGTAGCAGGTGAGCATCCAAGTCCATTTCCTC
CL-1            ACATATTGCAGGCTTGGTTGTAGCAGGTGAGCATCCTAGTCCATTCCCTT
CU-1            TCACATTGCTGGACTTGTCGTAGCTGGTGAGCATCCTAGTCCTTTCCCTC
                TCATATTGCTGGGTTAGTTGCTGCTGGAGAACATCCATCACCATTTCCTC
                TCATATCGCCGGGCTTGTTGTCGCTGGAGAATACCCCAATCCATTTCCAC
                CCATGTGGCAGGGCTTGTGGTAACTAATGAGCATGCCCATCCTTTCCCGC ACACTCATGTAGTAAGCTCAACTACACATAAAACTTTGCGTGGTCCAAGA
                ATGCTCATGTAGTAAGCTCTACAACCCACAAAACCTTACGTGGTCCAAGA
                ATGCTCATGTTGTAAGTTCTACTACACATAAAACTTTAAGAGGTCCAAGG
                ACGCACACATCGTAAGCTCAACCACACACAAAACCCTAAGAGGTCCTAGA
                ATGCACATGTTGTAACAACTACTACACATAAAACATTAAGAGTACCTAGA
                ATTGTGATATTGTAACCTCAACCACACACAAAACCTTGCGAGGTGCAAGA
                ATTGCCATGTGGTTTCAAGCACCACTCATAAGACTTTAAGAGGGCCTAGA GGTGGTATTATTATGACAAATGATGAAGAGCTTGCTAAAAAAATTAATTC
                GCGGTATCATCATGACTAATGATGAAGAGCTTGCTAAAAAAATTAATTC
                GGTGGGATTATTATGTGTAATGATGAAGAAATTGCTAAAAAGATAAATTC
                GGTGGAATTATTATGTGTAATGATGAAGAAATTGCTAAAAAAATTAATTC
                GGTGTACTTATTTAACAGATGATGAAGAGATTTCTAAAAAAATCAATTC
                GGCGGGATTATCCTCACAAATAACGAAGAAATCGCTACTAAAATAGATAA
                GGAGGGATTATTTTAACCAATGATGAAGAGATAGCGGCTAAGATTGATAA TGCGATTTTTCCAGGTATTCAAGGAGGACCATTAATGCAT
                AGCTATTTTTCCAGGTATCCAAGGAGGACAATTAATGCAT
                AGCAATTTTTCCAGGCATTCAAGGTGGACCATTAATGCAT
                TGCGATTTTTCCTGGAATTCAAGGAGGTCCTTTAATGCAT
                AGCAATTTTCCCAGGACTTCAAGGTGGACCATTAATGCAT
                AAGCGTATTTCCGGGACTTCAAGGTGGACCATTGATGCAT
                AGCGATTTTTCCAGGGACTCAAGGAGGTCCATTAATGCAT
                                          S2 primer
```

FIGURE 2
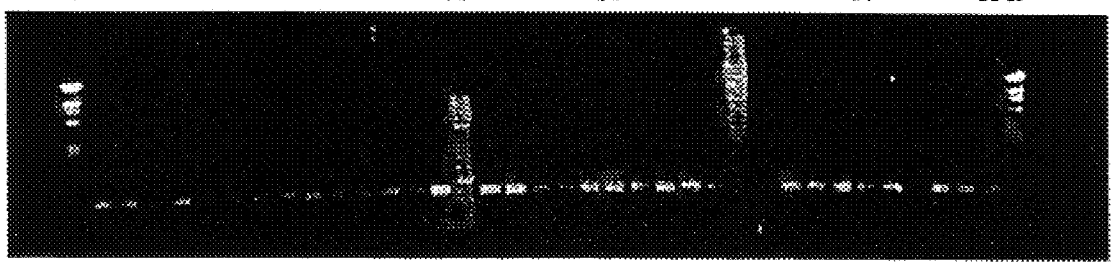
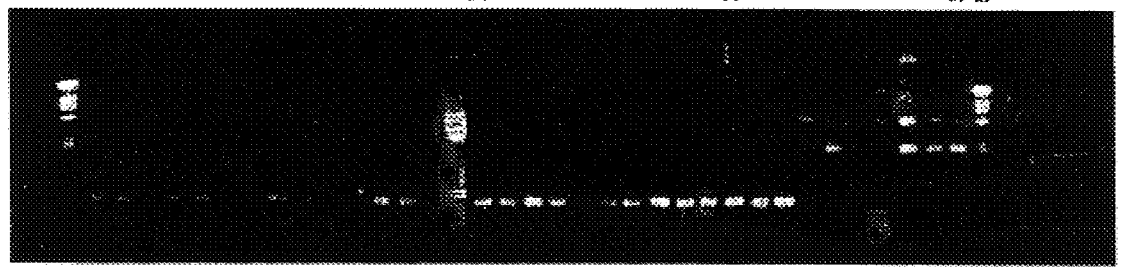

1 2 3 4 5 6 7 8 9 10 11 12 13

14 17 18 19 20 21 22 23 24 25 26 39

15 16 27 28 29 30 31 32    33 34 35 36 37 38 40 41

42 43 44 45 46 47 48 49 50 51 52 53 54 55

FIGURE 4
(A) 1 2 3 4 5 6 7 8 9 10 11 12 13
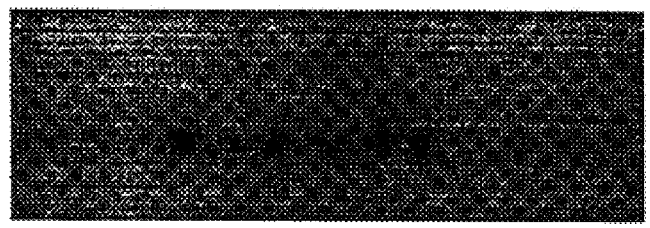
(B) 14    17 18 19 20 21 22 23 24 25 26    39
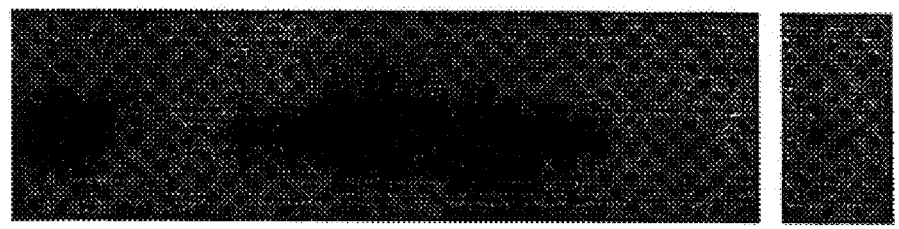
(C) 15 16    27 28 29 30 31 32 33 34 35    36 37 38    40 41
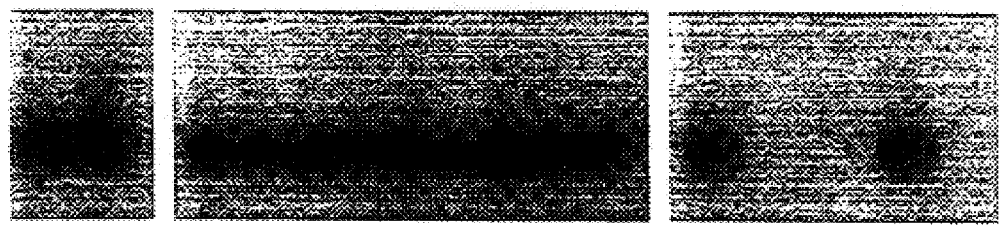
(D) 42 43 44 45 46 47 48    49 50 51 52 53 54 55
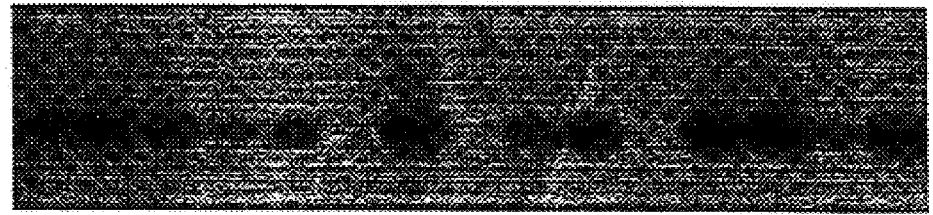

FIGURE 5
(A)
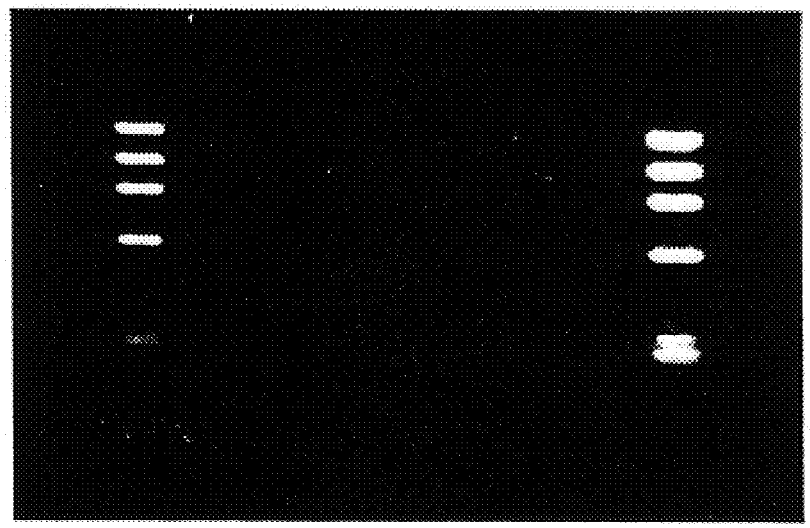
(B)
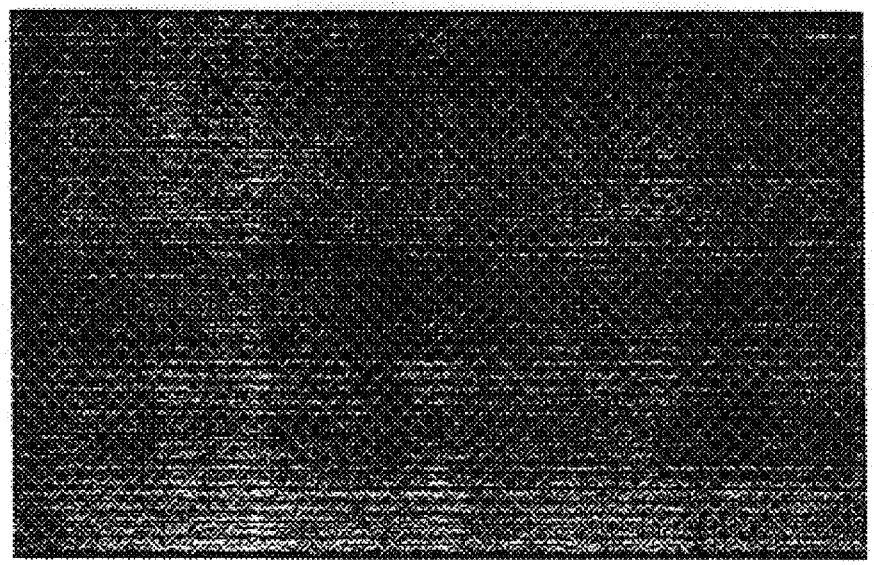

FIGURE 6A

```
C.jejuni     GTTGATGAGAGATTGAAACTCTAGCTATTGAAAGATGTAAAAACTTTTTAATTGTAAATTGCTAATGTTCAGCCTAATTCAGGTTCT
C.coli       GTAGATGAAATCGAAAATTTAGCTATAGAAGATGTAAAAGATGTAAAAACTTTTTAATTGTAGTTGCAAATGTCAACCTAATTCAGGTTCT
C.lari       GTAGATGAGATTGAAACGATTGCTATAGAAGATGCAAAAACTTTTTAATTGTAATTGCAATTGCAACCTAATTCAGGCTCG
CU #16672    GTTGATGAAATTGAAACTCTTGCTATCCAAAGATGCAAAAGATGCAAAAAACTCTTTAATTGTGCCTTTGCTAATGTCCAGCCAAATTCAGGCTCA
CU #14096    GTTGATGAAATTGAGACTCTTGCTATCCAAAGATGCAAAAGATGCAAAAAACTCTTTAATTGTGCCTTTGCTAATGTCCAGCAATTCAGGCTCA
A.nitrofig   GCTGATAAAGCAGAACAATTAGCAATTAGCAATAGAGAGCTTGTGAAATTTTGGTTGTGAAATTGCAAATGTACAACCTCATGCAGGTAGT
AB #13217    GCAGATAAAGTAGAACAATTAGCAATTAGCAATAGCAATGATGAGAGCTTGTGATGTAAATATGCAAATGTTCAACCACACTCAGGAAGC
AB #13218    GCTGATAAAGTAGAACAATTAGCAATTAGCAATGATGAGAGCTTGTGATGTAAATATGCAAATGTTCAACCACACTCAGGAAGC
BL #13432    GCTGATAAAGTAGAACAACTAGCAATTGACAGAGCTTGTAAAATATTGGATGTCTTATGCAAATGTTCAACCACATAGTGGATCT
BL #13207    GCTGATAAAGTAGAACAACTAGCAATTGATAGAGCTTGTAAAATATTTGGATGTTCTTATGCAAATGTTCAACCTCATGTGGAAGC
H.pylori     GTGGATAAAATAGAAAGCCTAGCTATAGAAAAGCCTAAAAAGCTTTCAATTGCCAGTGCCAAGCGCATTCAGGCTCA
H.cineadi    GTAGATAAAATCGAATCACTTGCTATTGAGCGCGTGAAGCAGCTATTTGGCTATGCAAATGTGCAGCCACATTCTGGCTCT
HC #16953    GTCGATGCAGTAGAGTCCATTGAGCGCGAGCTAAAAAGCTCTTTGGTGCGCGAAGTTTGCCAATGTGCAGCCACACTCTGGTAGC
HC #16485    GTCGATGCGATAGAATCCATAGCTATTGAGCGCGGCTAAAAAGCTCTTTAGTTGCAAATTTGCCAATGTGCAGCCACACTCTGGTAGC
             *   **     **  *     **       **     *      **   *    *   *    **  ** ***  *  *   **  *

C.jejuni     CAAGCTAATCAAGGTGTGTTTATGCGGCTTTGATTAATCCAGTGATAATCCAGTAAAAATTTAGGAATGGATTAAGTCATGGTGGACATTTAACT
C.coli       CAAGCTAATCAAGGCGTTTATGCTGCACTTTGATTAATCCAGTGATAATCCAGTGATAAAATTTAGGAATGATTAAGTCATGGTGGACATTTAACA
C.lari       CAAGCAAATCAAGGTGTGTATATGCTGCGCTTTATGCTGTTAAATCCAGTGATAGAATTTTGGGTATGGATTAAGCCATGGAGGACACTTGACT
CU #16672    CAAGCAAATCAAGGCGTTTATGCTGCGCTGCTTTATGCCTTAATGCAGGAGATAGAATTTTAGGTATGGATTTAAGCCACCACGGAGGACATCTTACA
CU #14096    CAAGCAAATCAAGGCGTTTATGCTGCGCTGCCTTTATGCCTTAATCAATGCAGGAGATAGAATCTTGGGTATGGATTTAAGCCAAGCACGGAGGACACCTTACA
A.nitrofig   CAAGCAAATGGTGTGCAGCAGTATATGCAGCAGCATTAGCAGCACTACTTAAGCAATTAATAAAAGCTGGTGATTAAGCTTAGGTATGGATTTAGACCCTTTAACT
AB #13217    CAAGCAAATGAGCAGCAGCATATGCAGCAGCATTAATAAGCAGCAGCAGCACTACTTAAGCAATTAAAATCTTAGGTATGGATTTATCTCATGGTGGACATTTAACT
AB #13218    CAAGCAAATGAGCAGCAGTATATGCAGCAGCATTAATAAGCAGCAGCACTACTTAAGCAATTAAAATCTTAGGTATGGATTATCTCATGGTGGACATTTAACT
BL #13432    CAAGCAAATGGTGCAGTTGCAGTTTGCAGCTTATGCAGCACTACTTAAAGCCTTAAAGCCTTAAAGCCATTAAAATATTAGGTATGGATCTCATCTCATGGTGGACATTTAACT
BL #13207    CAAGCAAATGGTGCAGTTGCAGTTATGCAGCTTATGCAGCAATGCACTACTTAAGCACTACTTAAAGCCTTAAAGCCTTAAAGCCTTAAAGCCATTAAAAATATTAGGTATGGATCTCATCTCATGGTGGACATTTAACT
H.pylori     CAAGCCAATAACGCTGTCTATCACGCGTATAATGCGCTTGCGTTGTGCGTTGCTTCAAGCCTCAAGCCTCAAGCCTCAAGCCTTAAAAGCCTTAAAAAGCTTAAAAGCTTAAGCCTTATGACAAGATTTTAGGCATGATTTAGGCATGTGGAGGGCATCATCTCACA
H.cineadi    CAAGCAAATGGCGCAGTCGCAGTTTATAATCTATAATGCACTAGCTTAAGCCTTATGGATCTAGGATCTAGGATCTAGGATCTAGATTCTAGGAATGATCTAAGCCATGGAATGATCTAAGCCATGGAATGATCTAAGCCATGGAATGATCTAAGCCATGGCATGGCCATGGCCATGGCATCATCTCACA
HC #16953    CAAGCAAATGGCGCAGTCGCAGTTTATGCAGTTATGCAGTTATGCACTTAAGCCTTAAGCCTTAAGCCTTAAGCCTTAGGATCTAGGATCTAGGATCTAGGATCTAGATCTAGGATCTAGGATCTAGGCTTAAGCCTTAAGCCTTAAGCCATGGCATGGCATGGCATCATCTACG
HC #16485    CAAGCAAATGGCGCAGTCGCAGTCTAAGCCTGTAGTGCGTTGCTGCTCAAGCCTCAAGCCTGTTGCTCAAGCCTATGACAAGATTTTGGGTATGGATCCTGACAAGATTTTGGGTATGGATCTAAGCCTTAAGCCTTAAGCCACCGGCCACCGGCCATCTCACA
             *****  ***     ***    **  * *         ***   *     *     *    *  *******    *****      **     ***
```

FIGURE 6B

```
C.jejuni      CATGGTGTGCAAAAGTAAGTTCTTCGGGTAAAATGTACGAAAGTTGTTTTTACGGCCGTAGAACTTGATGGAAGAATTGATTATGAAAAA
C.coli        CATGGTGCAAAAGTAAGTCATCGGGAAAAAATATATGAGAGCTTTTTTTATGGTGTTATGGAGAGCTTTATGGAAGGATAAACTATGAAAAA
C.lari        CATGGTTCTAAAAGTAAGTCTTCTGAAAAGTTCTTGGGTAAAATGTTTATGAAAGCTTGAGCTTGAGCTTGATGGAAGAATTAATTATGATAAA
CU #16672     CACGGAGCTAAGTTAGTAGCTCGGGTAAAATGTATGAAAGCTTTTTTTTATGGAGTTGAGTTGAGCTTGATGGGCGTATTAATTATGAAAAA
CU #14096     CACGGTGCTAAGGTTAGTAGCTCGGGTAAAATGTATGAAAGCTTTTTTTTATGGAGTTGAGTTGAGCTTGATGGGCGTATTAATTATGAAAAG
A.nitrofig    CATGGTTCTAAACCTTCATTTTCAGGAAAAATTATCAAGCATTTTATTATGGTGTAGAACTTGATGGTAGAATCAATTATGAGAAA
AB #13217     CATGGTTCTAAACCATCATCTCTGGACAAAATTATCAAGCATTCTATTATGGAGTTGAAGAATTAATTATGATAAA
AB #13218     CATGGTTCTAAACCATCATTTCTGGACAAAACTATCAAGCATTCTATTATGGAGTTGAAGAATTAATTATGATAAA
BL #13432     CATGGAAGTAAACCAAGCTTTTCAGGGCAAAACTACTCTCATTTTATTATGGTGTTGAAGAATTAATTATGATAAA
BL #13207     CATGGAAGTAAACCAAGCTTTTCAGGGCAAAACTACTCTGCATTTTACTATGGTGTTGAACTTGAACTTAACTATGATAAA
H.pylori      CATGGTGCTAAAGTGAGTTAACCGGCAAGCATTATCAGAGCTTTCTTATGGCCTGGGTTTGGATGGCTATATTGATTATGAAGAG
H.cineadi     CATGGCGCAAAAGTAAGTAAGTCATGCCAGGCAAGTGTATCAAAAGCTTTTTTTATGGCCTGTGGGCTTGAGCCAGGATAGATTATAATCAA
HC #16953     CACGGCGCGAAAGTAGCATTACAGGGCAGGTTATCAACATACAGAGATCTATCAAAAGCTTTTTTATGGCGTGTGGCGTAGATGGCAGGATTGATTACGACAAG
HC #16485     CACGGCGCGAAAGTGAGCATTGGACAGGACAGATCTATCAAAAGCTTTTTTTATGGCGTGTGGCGTAGATGGCAGGATTGATTATGAAAAG
                       *  *       **   *    *    *                *           *     ****      *

C.jejuni      GTAAGAGAGAAATTGCTAAAAAGAAAAAGCCAAATG-TAATAGTTTTGTGAGCTAGTGCTTATGCAAGAGTGATTGATTTGCTAAATT
C.coli        GTTAGGGAAATTGCTCATATTGTAAAACCAAAGC-TTATCGTGTCGTGCGCGTGCGAGTGCTTATGCTCGTATTCCTAGAGTGATTGACTTTCAAAATT
C.lari        GTTAGAGAGATAGCAAAAGAGATTAAACCAAAAC-TTATTGTTTGTGGTGCTGCGGGCAAGTGCTTATGCTTATCCTAGAGTGATTATTGATTTTGCTAAATT
CU #16672     GTAAGAGAGAAATAGCACACATCGTTAAGCCAAAC-TCATTGTATGCGGCAAGTGCTTATGCTAGGATTATGATTTTGCTAAATT
CU #14096     GTAAGAGAGATAGCTCATATTGTAACCCAAAAC-TCATTGTATGCGGGCAAGTGCTTATGCTTAGGATTATTGATTTTGCTAAATT
A.nitrofig    GTTATGGAAATAGCAAAAGTTACTATGCCAAAAATTATTGTTGTGGAGCAAA-GCTGACGCAAGCCAAGAAATTGATTTTGCTAAATT
AB #13217     GTTGAAGAGAGAAAAAGCATGTCAACCAAAAAA-TAATCGTTGTGGTGCTTCTGCATACGCAAGAGAATTGATTCAAAAGATT
AB #13218     GTTGAAGAGAGATAGCAAAAAATAGTTCAACCAAAAA-TAATCGTTGTGGTGCTTCTGCATACGCAAGAGAAATTGACTCAAAAGATT
BL #13432     GTTGAAGAGAGATAGCAAAATAGTTCAACCAAAAA-TAATCGTTGTGGTGCAAGTGCATATGCAAGAGAGATTGATTTAAAAGATT
BL #13207     GTGCAAGAGATTGCAAAATAGTACAACCAAAAA-TAATTGTTGTGGTGCAAGTGCATATGCAAGAGAGATTGACTTTAAAAGATT
H.pylori      GTAGAAGAGATAGTCATATTGTTCAACCTGTTAAGCCAAA-TCATTGTGTGCGGGTTTGCAGCCTATCCAAGGGAAATTGATTTTAAGAAATT
H.cineadi     ACGCTAAAATCGCTCAAGCGTTAAGCCAAAATAGTAGCAAACCTCGCC-TTATTGTGAACCCCAAAGA-TTTTGGTATGTGGGTTTTCTGCCTATACAAGAGACTAGATTTTGCCAAGTT
HC #16953     GTGCGAGAAATCGCAAAGCGCGTACTTGTGAAGCCAAAGA-TTTTGGTATGTGGGTTTTCTGCCTATACAAGAGACTAGATTTTGCCAAGTT
HC #16485     CTACGCCAAAAGTGCCACATATCATCAAGCACAAGA-TTTTGGTATGTGGATTGTGATTTCTGCCTATACAAGAGAGCTAGATTTTGCCAAGTT
               *  **      **            *   *   **    *     *   *     *  *  *  **      *   *
```

DNA PROBES FOR CAMPYLOBACTER, ARCOBACTER AND HELICOBACTER

This application claims benefit of Provisional Application 60/043,415 filed Apr. 8, 1997.

FIELD OF THE INVENTION

The invention relates to nucleotide probes that are useful in detecting and identifying bacterial pathogens. More particularly, the invention relates to nucleotide probes that are useful in detecting and identifying Campylobacter, Helicobacter and Arcobacter spp. bacterial pathogens.

BACKGROUND OF THE INVENTION

Campylobacter, Helicobacter, and Arcobacter spp. are examples of common human and animal pathogens (Thomas, C. A. et al., 1966). Although the pathogenicity of such bacteria has long been known, their phylogenetic relationships, isolation, detection, identification, and classification by traditional biochemical tests, have been variable and difficult. This is largely due to their fastidious growth requirements, inability to ferment carbohydrates, and diverse growth characteristics which vary, not only between genera and species, but also within species. Thus, their large phenotypic variations have made biochemical tests unreliable as a sole method for identifying and differentiating these bacteria.

Many of the species in the genera Helicobacter and Arcobacter were once classified under the genus Campylobacter. However, the phylogenetic relationships of these bacteria have been reevaluated based on information from DNA-DNA hybridization, 23S rRNA-DNA hybridization (Vandamme et al., 1991; Vandamme et al., 1993), and partial 16S rRNA sequences (Li et al., 1993; Patton et al., 1991; Totten et al., 1987). These phylogenetic studies have led to the formation of the current classification of the Campylobacter and Vibrio organisms into Campylobacter, Helicobacter, and Arcobacter.

Other than the conventional biochemical tests, alternative methods based on molecular and genetic approaches, have been proposed to improve the identification and differentiation of these bacteria to the species level. These methods include serology (Hebert et al., 1983; Penner, J. L., 1988), enzymology (Elharrif, Z. and Megraud, F., 1986; Paster et al., 1991), cellular fatty acid compositions (Goodwin et al., 1985), electrophoretic protein patterns (Costas et al., 1987; Penner, J. L., 1988), random PCR-DNA fingerprinting (Eyers et al., 1993; Giesendorf et al., 1993; Giesendorf et al., 1994; and Vandamme et al., 1992), and DNA-DNA hybridization (Macario, A. J. L. and Macario, E. C. de. (eds.), 1990; and Penner, J. L., 1988). A highly specific DNA-DNA hybridization method is oligo hybridization. By varying hybridization conditions such as ionic concentration and temperature, oligo probes can detect single nucleotide sequence differences (Lee/Lane, 1992).

SUMMARY OF THE INVENTION

The present inventors have developed a method for preparing nucleic acid probes for identifying species of bacterial pathogens, and have deceloped nucleic acid probes for identifying species of Campylobacter, Helicobacter and Arcobacter.

In particular, the inventors have identified several probes that are specific for the Campylobacter species, including *Campylobacter jejuni* (*C.jejuni*), *Campylobacter coli* (*C.coli*), *Campylobacter lari* (*C.lari*) and *Campylobacter upsaliens* (*C.upsaliens*); the Helicobacter species, including *Helicobacter cinaedi* (*H. cinaedi*); *Helicobacter pylori* (*H.pylori*); *Helicobacter canis* (*H. canis*); and the Arcobacter species, including *Arcobacter nitrofigalis* (*A.nitrofigalis*); *Arcobacter butzleri* (*A. butzleri*) and *Arcobacter butzleri-like* (*A. butzleri-like*).

The probes are useful in detecting the presence of a bacterial pathogen and are further useful in determining the identity of the specific pathogen.

In one aspect, the present invention relates to an isolated nucleic acid probe for detecting or identifying *C.jejuni*. In one embodiment the probe is designated CJATC-1 and has the sequence 5'-TTTTC CGCAC ACTCA TGTAG TAAGC TCAAC TA-3', and is identified as SEQ ID NO: 1. In another embodiment the probe is designated CJATC-2 and has the sequence 5'-GAAAA AGTAA GAGAA ATTGC TAAAA AAGAA-3', and is identified as SEQ ID NO: 2.

In another aspect, the present invention relates to an isolated nucleic acid probe for detecting or identifying *C. coli*. In one embodiment the probe is designated CC-1 and has the sequence 5'-ATTTC CTCAT GCTCA TGTAG TAAGC TCTAC AA-3', and is identified as SEQ ID NO: 3. In another embodiment the probe is designated CC-2 and has the sequence 5'-GAAAA AGTTA GGGAA ATTGC TCATA TTGTA-3', and is identified as SEQ ID NO: 4.

In another aspect, the present invention relates to an isolated nucleic acid probe for detecting or identifying *C. lari*. In one embodiment the probe is designated CL-1 and has the sequence 5'-ATTCC CTTAT GCTCA TGTTG TAAGT TCT-3', and is identified as SEQ ID NO:5. In another embodiment the probe is designated CL-2 and has the sequence 5'-GATAA AGTTA GAGAG ATAGC AAAAG AGATT-3', and is identified as SEQ ID NO: 6.

In another aspect, the present invention relates to an isolated nucleic acid probe for detecting or identifying *C. upsaliens*. In one embodiment the probe is designated CU-1 and has the sequence 5'-TTTCC CTCAC GCACA CATCG TAAGC TCA-3', and is identified as SEQ ID NO: 7. In another embodiment the probe is designated CU-2 and has the sequence 5'-GAAAA AGTAA GAGAA ATAGC ACACA TCGTT-3', and is identified as SEQ ID NO: 8. In a further embodiment the probe is designated GlyA-CU and has the sequence 5'-GGT TAG TAG CTC GGG TAA AAT GTA TGA AAG C-3' and is identified as SEQ ID NO: 15.

In another aspect, the present invention relates to an isolated nucleic acid probe for detecting or identifying *H. cinaedi*. In one embodiment the probe is designated HC-1 and has the sequence 5'-TGAGC GCGTG AAGCA GCTAT TTGGC TGTGC GT-3', and is identified as SEQ ID NO:9.

In another aspect, the present invention relates to an isolated nucleic acid probe for detecting or identifying *H.pylori*. In one embodiment the probe is designated HP-1 and has the sequence 5'-AGAAA GGGCT AAAAA GCTTT TCAAT TGCCA GT-3', and is identified as SEQ ID NO: 10.

In another aspect, the present invention relates to an isolated nucleic acid probe for detecting or identifying *H. canis*. In one embodiment the probe is designated GlyA-HC and has the sequence 5'-CAG GAT TGA TTA CGA CAA GCT ACG CCA AAG CGC GC-3' and is identified as SEQ ID NO: 16. In another embodiment the probe is designated GlyA-HC2 and has the sequence 5'-TTC TGC CTA TAC AAG AGA GCT AGA TTT TGC CAA G-3' and is identified as SEQ ID NO: 17.

In another aspect, the present invention relates to an isolated nucleic acid probe for detecting or identifying *A. nitrofigalis*. In one embodiment the probe is designated AN-1 and has the sequence 5'-AGATA GAGCT TGTGA AATTT TTGGT TGTAA AT-3', and is identified as SEQ ID NO: 11.

In another aspect, the present invention relates to an isolated nucleic acid probe for detecting or identifying *A.*

Butzleri. In one embodiment the probe is designated GlyA-AB and has the sequence 5'-GCT TCT GCA TAC GCA AGA GAA ATT GAT TCA AA- 3' and is identified as SEQ ID NO: 12.

In another aspect, the present invention relates to an isolated nucleic acid probe for detecting or identifying A. Butzleri-like. In one embodiment the probe is designated GlyA-BL and has the sequence 5'-GCA AGT GCA TAT GCA AGA GAG ATT GAT TTT AA-3' and is identified as SEQ ID NO: 13. In another embodiment the probe is designated GlyA-BL2 and has the sequence 5'-AAG TAA ACC AAG CTT TTC AGG GCA AAA CTA CTC T-3' and is identified as SEQ ID NO: 14.

The nucleic acid probes of the present invention permit the detection and identification of pathogenic bacteria in various samples including biological, food, or environmental samples.

Accordingly, the invention provides a method for detecting the presence of a specific bacteria in a sample comprising contacting the nucleic acid molecules of the sample with a nucleic acid probe according to the present invention and determining if the sample hybridizes with the nucleic acid probe.

The invention further provides a kit for detecting the presence of a specific bacteria in a sample comprising one or more nucleic acid probes according to the present invention, reagents required for hybridization of the nucleic acid probe with the nucleic acid molecules in the sample, and directions for its use.

Other features and advantages of the present invention will become apparent from the following detailed description.

It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 is a multiple nucleotide sequence alignment of the partial glyA sequences.

FIG. 2 shows PCR products of all species resolved in a 1% agarose gel and used in the Southern hybridization experiments.

FIG. 4 shows autoradiographs of the Southern hybridizations testing the species-specificity of the series 2 probes.

FIG. 5 shows sensitivity of the PCR/hybridization strategy.

FIG. 6 is a multiple nucleotide sequence alignment of the partial glyA sequences of Example 2.

DETAILED DESCRIPTION OF THE INVENTION

Figure 3A:
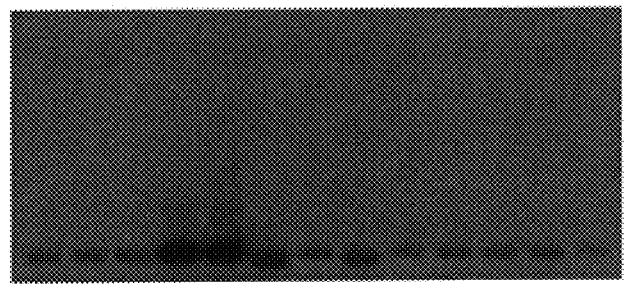
FIG. 3 shows autoradiographs of the Southern hybridizations testing the species-specificity of the series 1 probes.
Figure 3B:
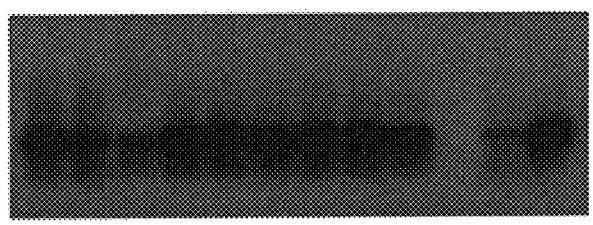
Figure 3C:
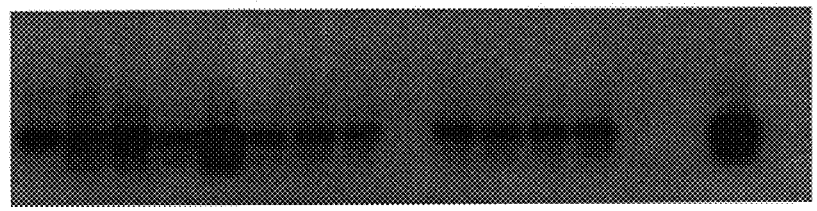
Figure 3D:
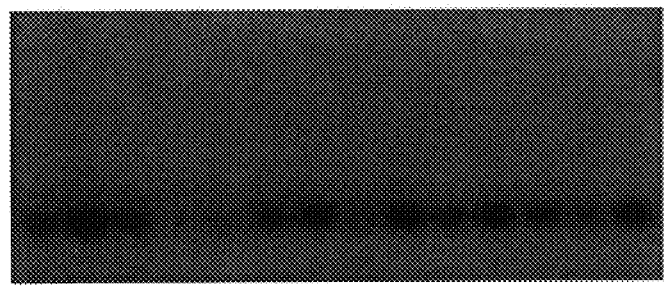
Figure 3E:
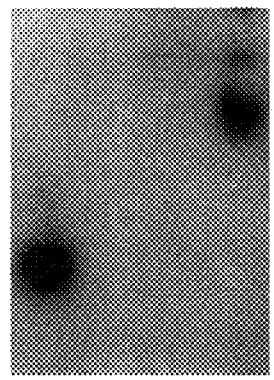
Figure 3F:
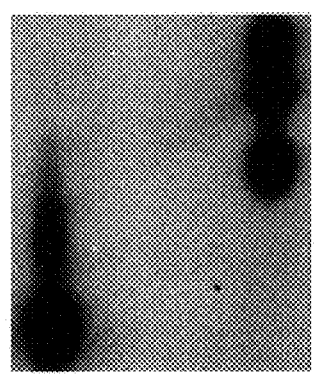
Figure 3G:
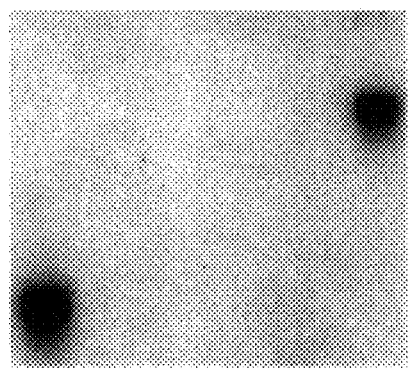

As mentioned above, the present invention provides a method for preparing nucleic acid probes for identifying species of bacterial pathogens, and it provides isolated nucleic acid probes which are useful in identifying and distinguishing between various bacteria including Campylobacter spp, Arcobacter spp., and Helicobacter spp.

As used herein, the term "isolated" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

In particular, the inventors have developed species specific oligonucleotide probes using the partial sequence of a specific conserved and essential gene, glyA which encodes serine hydroxymethyltransferase which is referred to herein as SHMT. To identify and differentiate closely-related species, a combined PCR-hybridization strategy was explored using these probes to target different regions within the glyA gene.

Degenerate oligodeoxyribonucleotides (oligos), designed by comparing the glyA gene sequences of *Campylobacter jejuni* (Chan, V. L. and Bingham, H., 1990) and *Escherichia coli* (Sambrook et al., 1989), were used in the polymerase chain reaction (PCR) to amplify a glyA fragment of approximately 640 base pairs (bps) from *C. jejuni* ATCC 33560, *C. coli* ATCC 33559, *C. lari* ATCC 35221, *C. upsaliensis* ATCC 43954, *Helicobacter cinaedi* ATCC 35683, *H. pylori* (clinical isolate), and *Arcobacter nitrofigilis* ATCC 33309. Alignment of the DNA sequences of these glyA fragments revealed three regions which were used to develop species-specific oligo probes. Two sets of probes targeting two regions of glyA were designed to detect and differentiate *C. jejuni, C. coli, C. lari,* and *C. upsaliensis*, which are designated CJATC-1, CC-1, CL-1, CU-1 for set 1, respectively, and CJATC-2, CC-2, CL-2, CU-2 for set 2, respectively. Another set of probes, targeting the third region, was designed to detect and differentiate *H. cinaedi, H. pylori,* and *A. nitrofigilis*. which are designated HC-1, HP-1 and AN-1, respectively. A further set of probes were designed to detect and differentiate *A. butzleri* (GlyA-AB); *A. butzleri*-like (GlyA-BL and GlyA-BL2); *Campylobacter upsaliensis* (GlyA-CU) and *Helicobacter canis* (GlyA-HC and GlyA-HC2). Using the hybridization and washing conditions described below, these probes were found to be species-specific. The probes of the present invention have the following nucleic acid sequences:

CJATC-1: 5'-TTTTC CGCAC ACTCA TGTAG TAAGC TCAAC TA-3' (SEQ ID NO: 1);

CJATC-2: 5'-GAAAA AGTAA GAGAA ATTGC TAAAA AAGAA-3' (SEQ ID NO: 2);

CC-1: 5'-ATTTC CTCAT GCTCA TGTAG TAAGC TCTAC AA-3' (SEQ ID NO: 3);

CC-2: 5'-GAAAA AGTTA GGGAA ATTGC TCATA TTGTA-3' (SEQ ID NO: 4);

CL-1: 5'-ATTCC CTTAT GCTCA TGTTG TAAGT TCT-3' (SEQ ID NO: 5);

CL-2: 5'-GATAA AGTTA GAGAG ATAGC AAAAG AGATT-3' (SEQ ID NO: 6);

CU-1: 5'-TTTCC CTCAC GCACA CATCG TAAGC TCA- 3' (SEQ ID NO: 7);

CU-2: 5'-GAAAA AGTAA GAGAA ATAGC ACACA TCGTT-3' (SEQ ID NO: 8);

HC-1: 5'-TGAGC GCGTG AAGCA GCTAT TTGGC TGTGC GT-3' (SEQ ID NO: 9);

HP-1: 5'-AGAAA GGGCT AAAAA GCTTT TCAAT TGCCA GT-3' (SEQ ID NO: 10);

AN-1: 5'-AGATA GAGCT TGTGA AATTT TTGGT TGTAA AT-3' (SEQ ID NO: 11);

GlyA-AB: 5'-GCT TCT GCA TAC GCA AGA GAA ATT GAT TCA AA- 3' (SEQ ID NO: 12);

GlyA-BL: 5'-GCA AGT GCA TAT GCA AGA GAG ATT GAT TTT AA-3' (SEQ ID NO: 13);

GlyA-BL2: 5'-AAG TAA ACC AAG CTT TTC AGG GCA AAA CTA CTC T-3' (SEQ ID NO: 14);

GlyA-CU: 5'-GGT TAG TAG CTC GGG TAA AAT GTA TGA AAG C-3' (SEQ ID NO: 15);

GlyA-HC: 5'-CAG GAT TGA TTA CGA CAA GCT ACG CCA AAG CGC GC-3' (SEQ ID NO: 16); and GlyA-HC2: 5'-TTC TGC CTA TAC AAG AGA GCT AGA TTT TGC CAA G-3' (SEQ ID NO: 17).

It will be appreciated that the invention includes probes that are complementary to the above probes. The invention also includes nucleic acids having substantial homology or identity with the nucleic acid sequences described above. The term "homologous" means probes that have nucleic acid sequences which have slight or inconsequential sequence variations from these sequences while maintaining their function as a species specific probe. The variations may be attributable to local mutations or structural modifications. The invention also includes nucleic acid probes that have been truncated or contain additional nucleotide sequences over the nucleic acid sequences described above.

The probes of the invention are useful in detecting and identifying bacteria in a sample including: biological materials, such as feces, blood or other bodily fluids or tissues from humans or animals such as mammals and poultry; in foods such as dairy products most particularly milk and poultry; and in environmental samples such as water and industrial wastes. The sample may be treated using techniques known in the art to render the nucleic acid molecules in the sample available to hybridize with the nucleic acid probes of the present invention. One sample may be assayed using several probes, either simultaneously or consecutively, in order to identify the species of the bacteria in the sample.

A nucleic acid probe of the present invention may be labelled with a detectable marker such as a radioactive label which provides for an adequate signal and has sufficient half-life such as $^{32}P$, $^{3}H$, $^{14}C$ or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

The nucleic acid probe may be used in solution (free) or may be bound to a solid support. Solid supports which may be used include polymeric supports such as polystyrene or agarose beads and filters such as nylon or nitrocellulose filters.

Accordingly, the present invention also relates to a method of detecting the presence of a specific bacteria in a sample by detecting a nucleic acid that hybridizes with a particular probe of the invention comprising contacting the sample under hybridization conditions with one or more of the nucleic acid probes of the invention and determining the degree of hybridization between the nucleic acid molecules in the sample and the nucleic acid probe(s).

Hybridization conditions which may be used in the method of the invention are known in the art and are described for example in Sambrook J, Fritch E F, Maniatis T. In: Molecular Cloning, A Laboratory Manual,1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

According to one embodiment the present invention provides a method for detecting the presence of a Campylobacter, Helicobacter or Arcobacter spp. bacteria in a sample comprising: (a) contacting the nucleic acid molecules of the sample, under hybridization conditions, with one or more nucleic acid probes selected from the group consisting of: CJATC-1 SEQ ID NO: 1; CJATC-2 SEQ ID NO: 2; CC-1 SEQ ID NO: 3; CC-2 SEQ ID NO: 4; CL-1 SEQ ID NO: 5; CL-2 SEQ ID NO: 6; CU-1 SEQ ID NO: 7; CU-2 SEQ ID NO: 8; HC-1 SEQ ID NO: 9; HP-1 SEQ ID NO: 10; AN-1 SEQ ID NO: 11; GlyA-AB SEQ ID NO 12; GlyA-BL SEQ ID NO 13; GlyA-BL2 SEQ ID NO 14; GlyA-CU SEQ ID NO 15; GlyA-HC SEQ ID NO 16; and GlyA-HC2 SEQ ID NO: 17; or nucleic acid sequences complementary or homologous to these sequences, and (b) determining if the nucleic acid molecules in the sample sample hybridizes with the nucleic acid probe(s).

According to another embodiment, the present invention provides a method for detecting C.jejuni in a sample by detecting a nucleic acid molecule in the sample that hybridizes with the nucleic acid probe CJATC-1 or CJATC-2, the method comprising contacting the sample under hybridization conditions with one or more of the nucleic acid probes CJATC-1 or CJATC-2, and determining the degree of hybridization between the nucleic acid molecule in the sample and the nucleic acid probe(s).

In another embodiment, the present invention provides a method for detecting C.coli in a sample by detecting a nucleic acid molecule in the sample that hybridizes with the nucleic acid probe CC-1 or CC-2, the method comprising contacting the sample under hybridization conditions with one or more of the nucleic acid probes CC-1 or CC-2, and determining the degree of hybridization between the nucleic acid molecule in the sample and the nucleic acid probe(s).

In a further embodiment, the present invention provides a method for detecting C.lari in a sample by detecting a nucleic acid molecule in the sample that hybridizes with the nucleic acid probe CL-1 or CL-2, the method comprising contacting the sample under hybridization conditions with one or more of the nucleic acid probes CL-1 or CL-2, and determining the degree of hybridization between the nucleic acid molecule in the sample and the nucleic acid probe(s).

In yet another embodiment, the present invention provides a method for detecting C.upsaliens in a sample by detecting a nucleic acid molecule in the sample that hybridizes with the nucleic acid probe CU-1, CU-2 or GlyA-CU, the method comprising contacting the sample under hybridization conditions with one or more of the nucleic acid probes CU-1, CU-2 or GlyA-CU, and determining the degree of hybridization between the nucleic acid molecule in the sample and the nucleic acid probe(s).

According to another embodiment, the present invention provides a method for detecting H.cinaedi in a sample by detecting a nucleic acid molecule in the sample that hybridizes with the nucleic acid probe HC-1, the method comprising contacting the sample under hybridization conditions with the nucleic acid probe HC-1, and determining the degree of hybridization between the nucleic acid molecule in the sample and the nucleic acid probe.

In another embodiment, the present invention provides a method for detecting H.pylori in a sample by detecting a nucleic acid molecule in the sample that hybridizes with the nucleic acid probe HP-1, the method comprising contacting the sample under hybridization conditions with the nucleic acid probe HP-1, and determining the degree of hybridization between the nucleic acid molecule in the sample and the nucleic acid probe.

In another embodiment, the present invention provides a method for detecting H. canis in a sample by detecting a nucleic acid molecule in the sample that hybridizes with the nucleic acid probe GlyA-HC or GlyA-HC2, the method comprising contacting the sample under hybridization conditions with the nucleic acid probe GlyA-HC or GlyA-HC2, and determining the degree of hybridization between the nucleic acid molecule in the sample and the nucleic acid probe.

In a further embodiment, the present invention provides a method for detecting A.nitrofigilis in a sample by detecting a nucleic acid molecule in the sample that hybridizes with the nucleic acid probe AN-1, the method comprising contacting the sample under hybridization conditions with the nucleic acid probe AN-1, and determining the degree of hybridization between the nucleic acid molecule in the sample and the nucleic acid probe.

In a further embodiment, the present invention provides a method for detecting A. butzleri in a sample by detecting a nucleic acid molecule in the sample that hybridizes with the nucleic acid probe GlyA-AB, the method comprising contacting the sample under hybridization conditions with the nucleic acid probe GlyA-AB, and determining the degree of hybridization between the nucleic acid molecule in the sample and the nucleic acid probe.

In a further embodiment, the present invention provides a method for detecting A. butzleri-like in a sample by detecting a nucleic acid molecule in the sample that hybridizes with the nucleic acid probe GlyA-BL or GlyA-BL2, the method comprising contacting the sample under hybridization conditions with the nucleic acid probe GlyA-BL or GlyA-BL2, and determining the degree of hybridization between the nucleic acid molecule in the sample and the nucleic acid probe.

According to another embodiment of the present invention there is provided a kit for detecting the presence of a Campylobacter, Helicobacter or Arcobacter bacteria in a sample comprising: (a) one or more nucleic acid probes selected from the group consisting of: CJATC-1 SEQ ID NO: 1; CJATC-2 SEQ ID NO: 2; CC-1 SEQ ID NO: 3; CC-2 SEQ ID NO: 4; CL-1 SEQ ID NO: 5; CL-2 SEQ ID NO: 6; CU-1 SEQ ID NO: 7; CU-2 SEQ ID NO: 8; HC-1 SEQ ID NO: 9; HP-1 SEQ ID NO: 10, AN-1 SEQ ID NO: 11; GlyA-AB SEQ ID NO 12; GlyA-BL SEQ ID NO 13; GlyA-BL2 SEQ ID NO 14; GlyA-CU SEQ ID NO 15; GlyA-HC SEQ ID NO 16; and GlyA-HC2 SEQ ID NO: 17; or nucleic acid sequences complementary or homologous to these sequences; (b) reagents required for hybridization of the nucleic acid probe with the nucleic acid molecules molecules in the sample; and (c) directions for its use.

According to a further embodiment, this kit can be used for identifying any one of Campylobacter jejuni (C. Jejuni), Campylobacter coli (C. coli), Campylobacter lari (C. lari) and Campylobacter upsaliens (C. upsaliens); Helicobacter cinaedi (H. cinaedi), Helicobacter pylori (H. pylori), Helicobacter canis (H. canis), Arcobacter nitrofigalis (A. nitrofigalis) Arcobacter butzleri (A. butzleri); and Arcobacter butzleri- like (A. butzleri-like) in a sample, the method comprising the method just mentioned and the further step of correlating the nucleic acid probe(s) which hybridize with the identity of the bacteria. This is discussed further below in the Discussion under the Examples.

By using the methodology described in the present application, one skilled in the art can readily isolate and identify specific probes from all of the other species of the Campylobacter, Helicobacter and Arcobacter species as well as other genera and other species of pathogenic bacteria. In particular, the glyA gene of other bacterial species or genera can be amplified using the oligonucleotide primers S1 and S2 (described herein) in the PCR. Other primers may also be prepared from the glyA sequences disclosed in FIGS. 1 and 6. In addition, the glyA gene can be sequenced from other bacterial genera and suitable nucleotide primers can be prepared.

Accordingly, the present invention provides the preparation of a nucleic acid probe that is specific for a particular species of bacteria comprising: (a) amplifying a glyA fragment from the bacteria using an oligonucleotide primer; (b) determining the nucleic acid sequence of the amplified fragment; (c) comparing the nucleic acid sequence of the amplified fragment with the nucleic acid sequence of glyA from one or more different bacterial species, and (d) identifying a nucleic acid sequence that is unique to the particular species of bacteria.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length.

Primers which may be used in the invention are oligonucleotides, i.e., molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al Nucl. Acid Res 4:2157, 1977) or automated techniques (See for example, Conolly, B A. Nucleic Acids Res. 15:15(7): 3131, 1987). The primers are capable of acting as a point of initiation of synthesis when placed under conditions which permit the synthesis of a primer extension product which is complementary to the DNA sequence of the invention, i.e., in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer may be single or double-stranded. When the primer is double-stranded it may be treated to separate its strands before using to prepare amplification products. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorcein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide sequence thereof, which is to be amplified. Restriction site linkers may also be incorporated into the primers allowing for digestion of the amplified products with the appropriate restriction enzymes facilitating cloning and sequencing of the amplified product.

PCR refers to a process for amplifying a target nucleic acid sequence as generally described in Innis et al, (Academic Press, 1990) in Mullis el al., (U.S. Pat. No. 4,863,195) and Mullis, (U.S. Pat. No. 4,683,202) which are incorporated herein by reference. Conditions for amplifying a nucleic acid template are described in M. A. Innis and D. H. Gelfand, (PCR Protocols, A Guide to Methods and Applications M. A. Innis, D. H. Gelfand, J. J. Sninsky and T. J. White eds, pp3–12, Academic Press 1989), which is also incorporated herein by reference.

The process described by Mullis amplifies any desired specific nucleotide sequence contained in a nucleic acid or mixture thereof. The process involves treating separate complementary strands of the nucleotide sequence to be amplified with two oligonucleotide primers which are extended under suitable conditions to form complementary primer extension products which act as templates for synthesizing the nucleotide sequence. The primers are selected so that they are sufficiently complementary to different strands of each specific nucleotide sequence to be amplified. The steps of the PCR reaction may be carried out sequentially or simultaneously and the steps may be repeated until the desired level of amplification is obtained.

The amplified products can be isolated and distinguished based on their respective sizes using techniques known in the art. For example, after amplification, the DNA sample can be separated on an agarose gel and visualized, after staining with ethidium bromide, under ultra violet (uv) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers. The detectable markers may be analyzed by restriction and electrophoretic separation or other techniques known in the art.

The conditions which may be employed in the methods of the invention using PCR are those which permit hybridization and amplification reactions to proceed in the presence of DNA in a sample and appropriate complementary hybridization primers. Conditions suitable for the polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp3–12, Academic Press 1989, which is incorporated herein by reference. Preferably, the PCR utilizes polymerase obtained from the thermophilic bacterium Thermus aquatics (Taq polymerase, GeneAmp Kit, Perkin Elmer Cetus) or other thermostable polymerase may be used to amplify DNA template strands.

It will be appreciated that other techniques such as the Ligase Chain Reaction (LCR) and NASBA may be used to amplify a nucleic acid molecule of the invention. In LCR, two primers which hybridize adjacent to each other on the target strand are ligated in the presence of the target strand to produce a complementary strand (Barney in "PCR Methods and Applications", August 1991, Vol.1(1), page 5, and European Published Application No. 0320308, published Jun. 14, 1989). NASBA is a continuous amplification method using two primers, one incorporating a promoter sequence recognized by an RNA polymerase and the second derived from the complementary sequence of the target sequence to the first primer (U.S. Ser. No. 5,130,238 to Malek).

The present invention also includes peptides encoded for by the nucleic acid probes of the present invention. Also included in the invention are antibodies that are specific for the peptides of the invention. Such antibodies may be useful in determining the identity of a bacterial pathogen in a sample. "Antibodies" used herein are understood to include polyclonal antibodies, monoclonal antibodies, antibody fragments (e.g., Fab' and F(ab')2 ) and recombinantly produced partners. Conventional methods can be used to prepare the antibodies. Monoclonal antibodies may be readily generated using conventional techniques (see U.S. Pat. Nos. RE 32,011, 4,902,614, 4,543,439, and 4,411,993 which are incorporated herein by reference; see also "Monoclonal Antibodies, Hybridomas: A New Dimension in Biological Analyses", Plenum Press, Kennett, McKearn, and Bechtol (eds.), Cold Spring Harbor Laboratory Press, 1988, and Goding, J. W., Monoclonal Antibodies: Principles and Practice, 2nd Ed., Academic Press, London, 1986 which are also incorporated herein by reference). Due to the small nature of the peptides they will generally be coupled to a carrier to increase their immunogenicity prior to immunization.

The following non-limiting examples are illustrative of the present invention:

EXAMPLES

Example 1

Bacterial strains, plasmids, and growth conditions used:

Bacterial strains used in this study are listed in Table 1. Campylobacter spp., Helicobacter spp., and *Arcobacter nitrofigilis* (Table 1) were grown on Columbia Agar Base (Oxoid) supplemented with defibrinated horse blood (5% final concentration). Campylobacter spp. and Helicobacter spp. were incubated at 37° C. from 24 to 48 hours and 36 to 72 hours, respectively, while *A. nitrofigilis* was incubated at room temperature (approximately 25° C.) for 24 to 48 hours. All species were grown in a 3 L anaerobic jar under microaerophilic conditions created by the Campylobacter Gas Generating Kit (Oxoid) which generates an atmosphere containing approximately 6% oxygen and 10% carbon dioxide.

For gene cloning experiments, plasmid pBluescript II KS+ (Stratagene) and *E. coli* strain JM101 (Sanger et al., 1977) were used. The *E. coli* cells were grown in Luria Bertani (LB) broth at 37° C. Competent cells were prepared by the rubidium chloride/calcium chloride protocol and transformed by standard procedures (Sanger et al., 1977). Transformants were grown on LB agar supplemented with ampicillin (100 ug/ml final concentration).

Extraction of genomic DNA:

Genomic DNA from Campylobacter spp. with the strain designations LMG, RG, and BVA (Table 1) was from P. Vandamme (Gent, Belgium). Genomic DNA from the remaining bacterial species was extracted as previously described (Thompson et al., 1988). Briefly, cultures grown on agar plates were scraped off and washed three times in 1XSSC (150 mM sodium chloride, 15 mM trisodium citrate, pH 7.0). For each wash, cells were centrifuged at 5000 rpm (GSA Sorvall rotor) for 5 minutes. Following centrifugation, the supernatant was decanted and the cell pellet was resuspended in 1XSSC. Finally, the washed cells were resuspended in 1XSSC containing 27% sucrose to a concentration of approximately $10^9$ cells per ml. Proteinase K was then added to a final concentration of 0.2 mg/ml and incubated at 60° C. for 1 hour. Genomic DNA was purified and extracted with an equal volume of buffer-saturated phenol (50 mM Tris.Cl, 10 mM EDTA, pH 8.0) with constant slow agitation for 30 mins at room temperature. The mixture was then chilled to 0° C. and centrifuged at 5000 rpm for 5 minutes. The phenol (top) phase was removed and the extraction was repeated. The aqueous DNA solution was dialyzed in 1.5 L of $T_{10}E_1$ (10 mM Tris.Cl, 1 mM EDTA, pH 8.0), three times, at 4° C. for 12 hours. The DNA was then precipitated with 0.3M sodium acetate pH 5.2 and two volumes of 95% ethanol for 12 hours at −20° C. The DNA was centrifuged for 30 minutes at 7000 rpm. The DNA pellet was redissolved in $T_{10}E_1$ and stored at 4° C.

Polymerase Chain Reaction (PCR):

A 640 bp region of the glyA gene was chosen to be amplified. It is directly flanked by conserved domains identified by amino acid sequence alignment of the *C. jejuni*, *E. coli* and available partial sequence of the rabbit SHMT homologue (Chan, V. L. and Bingham, H., 1990). This region also encompasses the domain implicated for binding the coenzyme, pyridoxal-5'-phosphate (Sambrook et al., 1989) and a domain that has been suggested to be part of the enzyme's active site (Innis et al. (eds.), 1990; Sambrook et al., 1989). The sequences of the two conserved flanking domains were used to synthesize degenerate oligo primers, S1 (5'-AA(C/T) AAA TA(C/A) GC(A/T) GAA GG(T/A) TAT- 3') and S2 (5'-ATG CAT (C/T)AA (A/T)GG (A/T)CC (A/T)CC TTG- 3'), to amplify the region of the glyA gene of the selected species. The PCR was performed on all the Campylobacter spp., the Helicobacter spp., *A. nitrofigilis, B. adolescentis, E. coli, L. casei, P. aeruginosa,* and *S. sonnei* (Table 1) using a thermal cycler (Perkin Elmer Cetus).

The PCR reactions were optimized at a concentration of 1 mM $MgCl_2$ for all species except for *A. nitrofigilis*, which was optimized at a concentration of 2 mM $MgCl_2$. The components of each 100 ul PCR reaction were 1 ug of genomic DNA (except for *H. pylori* for which 0.5 ug was used [as estimated from ethidium bromide stained agarose gels]), 20 pmoles of each primer, 20 umoles of deoxyribonucleotide triphosphates, 1X amplification buffer (10 mM Tris.Cl, 50 mM KCl, pH 8.3), and 2.5 units of Taq DNA polymerase (Promega and Boehringer Mannheim). The reaction solutions were overlaid with 100 ul of mineral oil to prevent any evaporation. The samples were subjected to 30 cycles of amplification, each of which consisted of template denaturation at 95° C. for 1.5 minutes, primer annealing at 42° C. for 2 minutes, and chain extension at 72° C. for 1 minute. After the 30 cycles, an additional extension step at 72° C. for 5 minutes was performed at the end of the reaction. The PCR products were purified from the deoxyribonucleotide triphosphates by passing the reaction solution through a Sephadex G-50 spun column (equilibrated in STE [10 mM Tris.Cl pH 7.5, 10 mM NaCl, 1 mM EDTA]). From each 100 ul PCR, 10 ul was subjected to electrophoresis in an ethidium bromide-stained 1% agarose gel, visualized under uv light illumination, and photographed.

To test the sensitivity of the PCR/hybridization method, serial dilutions of the *C. jejuni* ATCC 33560 genomic DNA template ranging from 1 fg to 1 ug were used in the PCR reactions.

Cloning, miniprep, and sequencing:

The PCR products of the Campylobacter spp., Helicobacter spp., and *A. nitrofigilis* (Table 1) were subcloned into pBluescript II KS+ at the EcoRV site and subsequently used to transform *E. coli* strain JM101 competent cells. Plasmid preparations (minipreps) were obtained and purified for sequencing using the alkaline lysis method (Sanger et al., 1977). The clones were sequenced by the Sanger dideoxy-chain termination method (Schirch et al., 1985) using the Sequenase Version 2.0 DNA sequencing kit (United States Biochemical) according to the manufacturer's recommendations. [alpha-$^{35}$S]-dATP (1000 Ci/mmole, ICN Biomedicals Canada Ltd.), and the M13(−20) forward and reverse primers (Stratagene) of pBluescript II KS+, and the PCR primers, S1 and S2, were used for the reactions.

DNA sequence alignment, probe designs, and syntheses:

The nucleotide sequences were analyzed using the Microgenie Sequence Analysis Program Version 5 (Beckman Instruments, Inc.) and Clustal V Multiple Alignment Program (Higgins et al., 1992; Higgins, D. G. and Sharp, P. M., 1989). Alignment of the partial glyA nucleotide sequences of *C. jejuni* ATCC 33560, *C. coli* ATCC 33559, *C. lari* ATCC 35221, *C. upsaliensis* ATCC 43954, *H. pylori* (clinical isolate), *H. cinaedi* ATCC 35683, and *A. nitrofigilis* ATCC 33309, identified 28 bp and 32 bp regions which were used to design the species-specific oligo probes CJATC-1, CC-1, CL-1, CU-1, HC-1, HP-1 and AN-1 (series 1 probes) (synthesized by Dalton Chemical Laboratories Incorporated), and CJATC-2, CC-2, CL-2 and CU-2 (series 2 probes) (synthesized by ACGT Corporated).

End-labelling of the probes:

The species-specific oligos were radioactively labeled in 20 ul reactions containing 20 pmoles of the oligos, 20 pmoles of [gamma-$^{32}$P]-ATP (4500 Ci/mmole, ICN Biomedicals Canada Ltd.), 1X Polynucleotide Kinase buffer (70 mM Tris.Cl pH 7.6, 10 mM $MgCl_2$, 5 mM dithiothreitol), and using 20 units of T4 Polynucleotide Kinase (Pharmacia and New England Biolabs). The reactions were incubated at 37° C. for 30 minutes and stopped by heating at 65° C. for 15 minutes. The radioactively-labeled probes were purified by passing the reaction solution through a STE equilibrated Sephadex G-50 spun column.

Southern blot:

HindIII-digested lambda phage DNA, 100 bp ladder DNA (Pharmacia), and pBluescript II KS+ vector (molecular weight markers and negative controls), glyA recombinant plasmid clones (positive control), and the PCR products from all the species examined were electrophoresed in a 1% agarose gel and transferred onto GeneScreen Plus nylon-based membranes (Du Pont Canada Inc.) by vacuum transfer using the LKB 2016 VacuGene Vacuum Blotting System (Pharmacia LKB Biotechnology). The transfer procedure consists of 15 minutes of depurination (2N HCl), 20 minutes of denaturation (1.5M NaCl, 0.5M NaOH), 20 minutes of neutralization (1.0M Tris.Cl, 2.0M NaCl, pH 5.0), and 1 hour of transfer (20XSSC - 3M NaCl, 0.3M trisodium citrate, pH 7.0) under a constant vacuum pressure of 55 $cm.H_2O$.

Southern hybridizations:

After Southern blotting, the membranes were air-dried at room temperature for 12 hours. Prior to hybridization, they were soaked in 2XSSC and prehybridized at 42° C. and 45° C. (for series 1 and 2 probes, respectively) for 30 minutes in 10 ml of prehybridization solution (1% SDS, 1M NaCl, 10% dextran sulfate, and 5 mg/ml denatured sheared salmon sperm DNA. Then, the labeled probe was added with a specific activity of $3 \times 10^5$ cpm/ml and the hybridization was done at 42° C. and 45° C. (for series 1 and 2 probes, respectively) for 8 to 24 hours. This was followed by two washes, each with 0.2XSSC at 60° C. and 50° C. (for series 1 and 2 probes, respectively) for 10 minutes with constant agitation. Bands were visualized by autoradiography using X-ray films (X-OMAT AR, Kodak Scientific Imaging Film) exposed to the membranes for 40 minutes to 10 hours at room temperature and also, 10 to 20 hours at −70° C.

RESULTS

DNA sequences and alignment—species-specific oligo probes. The complete sequences were obtained by merging the sequences from both ends of the subcloned glyA fragment. Two independent glyA recombinant clones of each species were sequenced to ensure the accuracy of the sequences.

Three regions were chosen to design species-specific rather than genus-specific probes. The first set of oligo probes to detect *C. jejuni, C. coli, C. lari,* and *C. upsaliensis* were designed from the region suggested to be part of the active site of SHMT (Innis et al., 1990; Sanger et al., 1977), while the oligo probes to detect *H. cinaedi, H. pylori,* and *A. nitrofigilis* were designed from a region with high sequence variation located downstream of the conserved domain targeted by the degenerate S1 oligo. The second set of oligo probes to detect the four Campylobacter spp. were designed from another region of variable sequences which is adjacent to the conserved domain implicated for binding to the co-enzyme,pyridoxal-5'-phosphate (Sanger et al., 1977). The sequences of the species-specific single-stranded oligo probes (FIG. 1) are:

CJATC-1: 5'-TTTTC CGCAC ACTCA TGTAG TAAGC TCAAC TA-3' (SEQ ID NO: 1);

CJATC-2: 5'-GAAAA AGTAA GAGAA ATTGC TAAAA AAGAA-3' (SEQ ID NO: 2);

CC-1: 5'-ATTTC CTCAT GCTCA TGTAG TAAGC TCTAC AA-3' (SEQ ID NO: 3);

CC-2: 5'-GAAAA AGTTA GGGAA ATTGC TCATA TTGTA-3' (SEQ ID NO: 4);

CL-1: 5'-ATTCC CTTAT GCTCA TGTTG TAAGT TCT-3' (SEQ ID NO: 5);

CL-2: 5'-GATAA AGTTA GAGAG ATAGC AAAAG AGATT-3' (SEQ ID NO: 6);

CU-1: 5'-TTTCC CTCAC GCACA CATCG TAAGC TCA-3' (SEQ ID NO: 7);

CU-2: 5'-GAAAA AGTAA GAGAA ATAGC ACACA TCGTT-3' (SEQ ID NO: 8);

HC-1: 5'-TGAGC GCGTG AAGCA GCTAT TTGGC TGTGC GT-3' (SEQ ID NO: 9);

HP-1: 5'-AGAAA GGGCT AAAAA GCTTT TCAAT TGCCA GT-3' (SEQ ID NO: 10);

AN-1: 5'-AGATA GAGCT TGTGA AATTT TTGGT TGTAA AT-3' (SEQ ID NO: 11).

The series 1 set of probes has a $T_m$ range from 60.5° C. (for AN-1) to 72.1° C. (for HC-1) while the series 2 set of probes has a $T_m$ range from 54.9° C. (for CJATC-2) to 59.3° C. (for CU-2). The conditions for hybridization and washing were optimized to select for species-specific hybridizations. Thus, two stringent conditions were used based on the melting temperatures of the two series of probes.

Each probe's species-specificity was tested against the bacteria listed in Table 1. This was done by PCR amplifying the glyA fragments using genomic DNA from all the species including all the Campylobacter spp., Helicobacter spp., *A. nitrofigilis, B. adolescentis, E. coli, L. casei, P. aeruginosa,* and *S. sonnei* (FIG. 5). However, no PCR products were obtained from *B. adolescentis* and *L. casei* (data not shown). In addition, pBluescript II KS+ and the recombinant plasmids that were sequenced, were used in the hybridizations as negative and positive controls, respectively.

The results of the hybridizations are shown in FIG. 3, panels (A) to (G) for the series 1 set of probes and in FIG. 4 panels (A) to (D) for the series 2 set of probes. The CC-1, CU-1, HC-1, HP-1, and AN-1 probes are species-specific under the hybridization and washing conditions since exposure times between 40 minutes to 20 hours did not show cross-species hybridization. While the CJATC-1 and CL-1 probes appear to be species-specific after exposure times between 40 minutes to 4 hours, there is some cross-hybridization that can be detected after 18 to 20 hours of exposure. The CJATC-1 probe cross-hybridized to the PCR products of *C. coli* and the CL-1 probe cross-hybridized to the PCR products of *A. nitrofigilis*. The CC-2 probe is species-specific under these hybridization and washing conditions since cross-hybridization to the other species' PCR products is not seen after exposure times of up to 22 hours. The CJATC-2, CL-2, and CU-2 probes also are species-specific after 4 hours of exposure. However, there is some cross-hybridization that can be observed after exposure of 22 hours. The CJATC-2 and CL-2 probes cross-hybridized to the PCR products of some *C. upsaliensis* strains, while the CU-2 probe cross-hybridized to the PCR products of some *C. jejuni* strains.

Detection of different strains and serotypes. The ability of the *C. jejuni, C. coli, C. lari,* and *C. upsaliensis* probes to hybridize to different strains and serotypes of the species was also tested. FIGS. 3 and 4 (see the "(A)" panels in each) show that CJATC-1 and CJATC-2 probes are able to detect 12 other strains and serotypes of *C jejuni*; the "(B)" panels in FIGS. 3 and 4 show that CC-1 and CC-2 probes are able to detect 9 other *C. coli* strains; FIGS. 3 and 4 (see the "(C)" panels) show that CL-1 and CL-2 probes are able to detect 13 other strains; and the "(D)" panels in FIGS. 3 and 4 show that CU-1 and CU-2 probes are able to detect 13 other *C. upsaliensis* strains.

Sensitivity. The PCR using the S1 and S2 oligos was performed on serially diluted *C. jejuni* ATCC 33560 genomic DNA to determine the amplification yield and ultimately, the sensitivity of this PCR/hybridization approach. The CJATC-1 probe was tested for its ability to detect the lowest amount of the PCR product. The results in FIG. 5 show that the lowest amount of genomic DNA required in order to yield enough PCR product to be detected by the CJATC-1 probe is 4 picograms ($4\times10^{-12}$ grams).

DISCUSSION

Species-specific oligos were designed from the aligned glyA sequences and their specificity was tested by subsequent hybridizations. PCR products were isolated from all the Campylobacter, Helicobacter, and Arcobacter spp. and from *E. coli, P. aeruginosa,* and *S. sonnei*.

From the hybridization results, the CC-1, CU-1, HC-1, HP-1, and AN-1 probes are species-specific under these hybridization and washing conditions since exposure times of up to 20 hrs did not detect any cross-hybridization with any of the other species. However, the CJATC-1 probe cross-hybridized to the PCR products of *C. coli*, and the CL-1 probe cross-hybridized to the PCR products of *A. nitrofigilis* when exposed for greater than 18 hours.

The second set of probes were tested using different hybridization and washing conditions. The results demonstrate that the CC-2 probe is species-specific since exposure of up to 22 hours did not reveal any cross-hybridization to any of the other species. However, both the CJATC-2 and CL-2 probes cross-hybridized to the PCR products of some *C. upsaliensis* strains, and the CU-2 probe cross-hybridized to the PCR products of some *C. jejuni* strains with longer exposure times (e.g. 22 hours).

Since an unknown sample may contain any one of the species, the use of diagnostic set 1 or 2 (Table 2) would resolve the discrepancies due to cross-hybridization. For example, using diagnostic set 1, if an unknown sample was detected by both CJATC-1 and CC-1, since CJATC-1 cross-hybridizes weakly to *C. coli* and CC-1 only detects *C. coli*, the sample would be determined as *C. coli*. However, if the unknown sample would be detected by CJATC-1 but not by CC-1, then by the same deduction, the sample is determined as *C. jejuni*. Thus, cross-hybridizations would not be a factor for misidentification. Furthermore, cross-hybridization would not affect the identification of either *C. jejuni* or *C. lari* strains since the *C. jejuni* probes do not cross-hybridize to the *C. lari* glyA PCR fragments and vice versa.

The CJATC-1, CJATC-2, CC-1, CC-2, CL-1, CL-2, CU-1, and CU-2 probes could also detect different strains of their various respective species. However, the strength of the hybridizations were varied. This may be due to minor nucleotide sequence variations between the different strains, which were observed when the glyA sequences of *C. jejuni* ATCC 43431 (Chan, V. L. and Bingham, H., 1990) and *C. jejuni* ATCC 33560 were aligned (data not shown). From the sequence alignment analysis, *C. jejuni* ATCC 43431 and *C. jejuni* ATCC 33560 vary by 2 nucleotides at the CJATC-1 target sequence. None of the probes hybridized to the other bacterial species such as *C. sputorum* subsp. *bubulus, E. coli, P. aeruginosa,* and *S. sonnei*.

The sensitivity of this PCR/oligo hybridization strategy was determined by using the CJATC-1 probe targetting *C. jejuni* ATCC 33560 as the test species. The lowest amount of genomic DNA required to yield sufficient PCR product which could be detected by CJATC-1 was 4 picograms ($4\times10^{-12}$ grams). Since the *C. jejuni* chromosome is approximately $1.8\times10^6$ bps, $4\times10^{-12}$ grams corresponds to approximately 2062 copies of template. However, the result that was detected was of 10 ul of the total 100 ul reaction volume. Therefore, the PCR would be able to amplify detectable amounts of product from approximately 200 copies of template.

While isotopic detection systems may have disadvantages (e.g. isotopic decay, radiation exposure, etc.), this PCR/hybridization strategy can be used as a rapid diagnostic method for detecting the various species of Campylobacter, Helicobacter, and Arcobacter. Five hours could be used as the minimum exposure time for species-specific identification. This exposure time would not reveal the cross-hybridizing bands. However, as previously mentioned, the probes detect different strains of the same species with varying signal intensities. Therefore, a further exposure, such as ten hours, could also be done to detect different strains without the appearance of cross-hybridizations. In addition, simultaneous use of a combination of the CC-1, CC-2, CU-1, HC-1, HP-1, and AN-1 probes with the CJATC-1, CJATC-2, CL-1, CL-2, and CU-2 probes (e.g. diagnostic set 1 or 2, ref. Table 2) would significantly reduce the likelihood of misidentifications due to cross-hybridizations. With the current conditions and limited exposure times, however, all the probes that have been designed are species-specific and could identify and differentiate the Campylobacter, Helicobacter, and Arcobacter spp. that were studied.

Example 2

Bacterial strains and its growth conditions

Bacterial strains used in this study are listed in Table 3. 10 strains each of *Arcobacter butzleri, Arcobacter butzleri*-like, *Campylobacter upsaliensis,* and 3 strains of *Helicobacter canis* were from LCDC. *Campylobacter jejuni, Campylobacter coli, Acrobacter nitrofigilis, Helicobacter cinaedi, Shigella sonnei, Escherichia coli,* and *Pseudomonas aeruginosa* were from the American Type Culture Collection (ATCC), Rockville, USA. *Campylobacter lari* was from Dr. J. L. Penner, University of Toronto, Toronto, Ontario, Canada. *Helicobacter pylori* is a clinical isolate from Mount Sinai Hospital, Toronto, Ontario, Canada. The Arcobacter, Campylobacter, and Helicobacter were grown on Mueller Hinton agar supplemented with 10% sheep's defibrinated blood, incubated at 37° C. from 2 to 6 days in a 2.5 L anaerobic jar under microaerophilic conditions created by the Campylobacter Gas Generating Kit (Oxoid).

Genomic DNA Extraction

Bacterial cells were collected and genomic DNA isolated with the DNAzol Reagent (Gibco BRL). Cells from a densely grown plate were lysed for 10 minutes at room temperature with 1 ml of DNAzol reagent, followed by centrifugation at 13,000 rpm for 10 minutes at 4° C. DNA in the supernatant was precipitated by the addition of 0.5 ml of 100% ethanol and placed on ice for 20 minutes. DNA was pelleted at 13,000 rpm for 20 minutes at 4° C. The DNA precipitate was washed twice with 95% ethanol, dried under vacuum and resuspended in 200 ul 8 mM NaOH for 48 hours. The pH was adjusted to 7.5 with the addition of 18 ul of 1M HEPES (free acid). DNA was quantified by optical density readings at 260 nm and 280 nm.

Polymerase Chain Reaction

Three degenerate oligo primers, S1 [5'-AA(C/T) AAA TA(C/A) GC(A/T) GAA GG(T/A) TAT- 3'], S2 [5'-ATG CAT (C/T)AA (A/T)GG (A/T)CC (A/T)CC TTG 3'] and S5 [5'-C(G/T)G C(G/A)A T(G/A)T G (G/A)G CAA TAT C(A/T)G C- 3'], were designed based on sequences on the conserved regions of glyA so that a 640 bp PCR product could be amplified with S1 and S2 and a 460 bp product with S1 and S5. The reaction was optimized at 1.5 mM of MgCl$_2$ for all samples. A 50 ul PCR reaction contained 0.4 ug of genomic DNA, 50 pmoles of each primers, 10 umoles each of the four deoxyribonucleotide triphosphates, 1X amplification buffer (20 mM Tris-HCl, 50 mM KCl, pH 8.4), and 2.5 units of Taq DNA polymerase (Boehringer Mannheim). The samples were overlay with 50 ul of light mineral oil and amplified for 30 cycles in a thermal cycler (Perkin Elmer Cetus) with an initial denaturation at 95° C. for 3 minutes. Each cycle consisted of denaturation at 95° C. for 1.5 minutes, annealing of primers at 48° C. for 2 minutes and extension at 72° C. for 1 minute. After the standard 30 cycle PCR amplification reaction, an additional extension step at 72° C. for 10 minutes was performed. 2.5 ul of the amplified products were ran in a 1.5% agarose gel, stained with ethidium bromide and visualized on an UV light illuminator.

Sequencing of PCR Products

The amplified products of two strains from each species of *Arcobacter butzleri, Arcobacter butzleri*-like, *Campylobacter upsaliensis* and *Helicobacter canis* were obtained by the standard PCR reaction using S1 and S2 oligo primers. Each PCR product was passed through a MicroSpin S-400 HR column (Pharmacia Biotech). 5 ul of the products were used for sequencing in an Ampli-Cycle Sequencing Kit (Perkin Elmer). Briefly, the 30 ul reaction consisted of 5 ul of DNA template, 20 pmoles of oligo primers, S1, S2 or an internal primer [GlyA-In1 (5'-GAT AAA ATA TTA GGT ATG- 3')], 5 uCi of [a $^{32}$P] dATP, 5 ul of 20 uM dATP/dTTP mix, and 4 ul of 10X cycling mix. 6.5 ul of the mixture is combined with 2 ul of each of the termination mixes and overlaid with 20 ul of light mineral oil. The sequencing was performed in a 25-cycle reaction, with a denaturation at 95° C. for 1 minute, annealing of primers at 45° C. for 1 minute and extension at 72° C. for 1 minute. At the end of the cycling reaction, 4 ul of stop buffer was added and samples were heated at 94° C. for 3 minutes prior to loading onto a 6% polyacrylamide sequencing gel.

DNA Sequence Alignment and Probe Design

The nucleotide sequences were analysis with DNAsis (Helix Corporation) and aligned with Clustal W Multiple Alignment program (Higgins et al., 1992; Higgins and Sharp et al. 1989). The partial glyA sequences of two strains of *Arcobacter butzleri, Arcobacter butzleri*-like, *Campylobacter upsaliensis* and *Helicobacter canis,* were aligned with other Campylobacter, Arcobacter, and Helicobacter sequences (sequenced by Shahnaz Al Rashid from Dr. V. L. Chan's lab). 31–35 mer oligo probes were designed for each of the four groups of bacteria and tested for their specificity.

End-labeling of the Oligo Probes

The oligo probes were radioactively labeled in 30 ul reaction consisting of 50 pmoles of oligo, 25 uCi of [g $^{32}$P] ATP, 1X T4 polynucleotide kinase buffer (70 mM Tris-HCl, 10 mM MgCl$_2$, 5 mM DTT, pH 7.6 @25° C.), and 20 units of T4 polynucleotide kinase (Pharmacia Biotech). The reactions were incubated at 37° C. for 30 minutes and stopped by heating at 65° C. for 10 minutes. The radioactively labeled probes were passed through a Sephadex G-25 MicroSpin column (Pharmacia Biotech).

Southern Blot

The PCR products from all the bacteria listed in Table 3, along with 100 bp ladder (Pharmacia Biotech) were electrophoresed in a 1.5-% agarose gel and transferred to Hybond membrane (Amersham) by capillary actions. The blot consisted of depurination (0.25N HCl) for 30 minutes, denaturation for 30 minutes (0.4N NaOH and 0.6N NaCl) and neutralization for 30 minutes (0.5M Tris-HCl pH 7.5 and 1.5M NaCl). The DNA was transferred overnight in 10X SSC (1.5M NaCl, 0.15M trisodium citrate, pH 7.0).

Southern Hybridization

After blotting, the filters were air-dried at room temperature for 3 hours. The filters were prehybridized at 37° C. for 30 minutes with 10 ml of prehybridization solution (50% formamide, 1M NaCl, 1% ultra-pure SDS, 10% dextran sulfate). The labeled probe was added to a specific activity of 1×10$^6$ cpm/ml and hybridized overnight at 37° C. for. The filters were washed from 55° C. to 64° C. in 0.2X SSC, 1% SDS for 15 minutes with constant agitation. DNA hybrid bands were visualized by autoradiography using X-ray film (X-OMAT AR, Kodak Scientific Imaging Film) with 2 hours to overnight exposure at room temperature.

RESULTS

DNA Sequence Alignment and Species Specific Oligo Probes

The sequences of *Arcobacter butzleri, Arcobacter butzleri*-like, *Campylobacter upsaliensis* and *Helicobacter canis,* were obtained by merging the sequencing result of S1, S2 and GlyA-In1 primers. The sequences were compared among each other and the percentages of identity of the nucleotides are shown in Table 4. The other Campylobacter, Arcobacter, and Helicobacter sequences seen in the multiple alignment (FIG. 6) were from Dr. V. L. Chan's lab. The species-specific oligo probes (Table 5) were designed for *Arcobacter butzleri*, *Arcobacter butzleri*-like, *Campylobacter upsaliensis* and *Helicobacter canis* were based on information from the sequences and the multiple aligrnnent and are as follows:

GlyA-AB: 5'-GCT TCT GCA TAC GCA AGA GAA ATT GAT TCA AA- 3' (SEQ ID NO: 12);
GlyA-BL: 5'-GCA AGT GCA TAT GCA AGA GAG ATT GAT TTT AA-3' (SEQ ID NO: 13);
GlyA-BL2: 5'-AAG TAA ACC AAG CTT TTC AGG GCA AAA CTA CTC T-3' (SEQ ID NO: 14);
GlyA-CU: 5'-GGT TAG TAG CTC GGG TAA AAT GTA TGA AAG C-3' (SEQ ID NO: 15);
GlyA-HC: 5'-CAG GAT TGA TTA CGA CAA GCT ACG CCA AAG CGC GC-3' (SEQ ID NO: 16); and
GlyA-HC2: 5'-TTC TGC CTA TAC AAG AGA GCT AGA TTT TGC CAA G-3' (SEQ ID NO: 17)

Southern Blot and Hybridization

Figure 8:
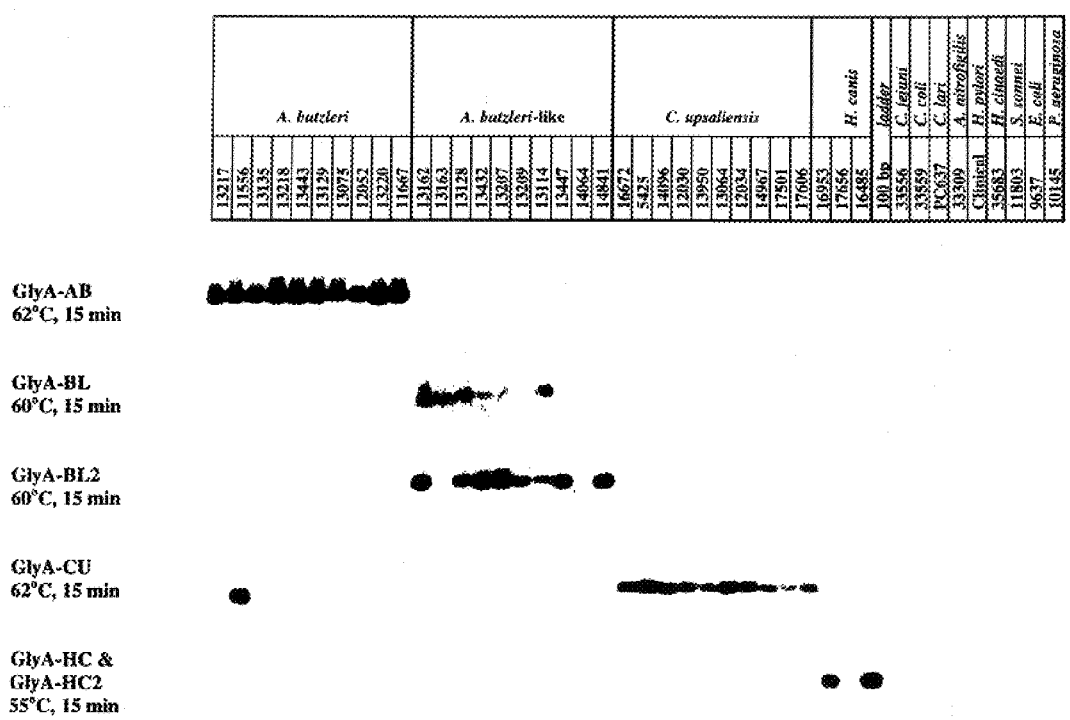
FIG. 8 shows the hybridization results with each of the species-specific oligo probes used in Example 2.

The 33 strains of *Arcobacter butzleri*, *Arcobacter butzleri*-like, *Campylobacter upsaliensis* and *Helicobacter canis* supplied by LCDC were amplified with S1 and S5 primers. The remaining species were negative controls amplified with S1 and S2 primers (supplied by Shahnaz Al Rashid from Dr. V. L. Chan's lab). The gel was blotted and hybridized to the species-specific probes. The results of the hybridizations are shown in FIG. 8.

The *A.butzleri* species-specific probe, GlyA-AB, was able to detect all 10 strains of *A.butzleri*. No cross hybridization was detected with 4 hours of exposure time. However, GlyA-AB did hybridize weakly with *Arcobacter butzleri*-like strains with exposure time exceeding 4 hours and with *A.nitrofiglis* with exposure time exceeding 20 hours. The *Arcobacter butzleri*-like probe, GlyA-BL, was able to detect 6 *A.butzleri*-like strains with no cross hybridization detected after 20 hours of film exposure. The second *Arcobacter butzleri*-like probe, GlyA-BL2, was able to strongly hybridize to 6 and weakly hybridize to 2 of the *Arcobacter butzleri*-like strains after 4 hours of film exposure. No cross hybridization was observed after 20 hours of exposure with GlyA-BL2.

The *Campylobacter upsaliensis* species-specific probe, GlyA-CU, hybridized to all 10 *C. upsaliensis* strains along with *Arcobacter butzleri* strain reference #11556. The hybridization was repeated with two other *C. upsaliensis* oligo probes (previously developed by Shahnaz Al Rashid) and *Arcobacter butzleri* reference #11556 was detected by all three probes. GlyA-CU was specific and did not have any cross-species hybridization with 4 hours of exposure time. But overnight exposure did reveal a weak hybridization to *C. jejuni*, *C. coli*, *C. lari*, and *H. canis* reference #16485. The *Helicobacter canis* species-specific probes, GlyA-HC and GlyA-HC2, both detected only 2 strains of *H. canis*. Both probes did not cross react with any other species with exposure time exceeding 24 hours.

Sensitivity of Oligo Probes

The genomic DNA of *A. butzleri* ATCC 49616, *A. butzleri*-like reference #13162, *C. upsaliensis* ATCC 43954, and *H. canis* ATCC 51401 were serially diluted 10-fold in order to determine the sensitivity of the oligo probes. GlyA-AB was able of detecting one-half of the PCR products of 100 pg, corresponding approximately to 46,000 copies of genomic DNA of *A. butzleri* ATCC 49616. GlyA-BL and GlyA-BL2 both detected one-half of the PCR products of 1 ng or 460,000 copies of genomic DNA from *A. butzleri*-like reference #13162. Similarly, GlyA-CU was capable of detection 1 pg or 460 copies of genomic template. GlyA-HC and GlyA-HC2 both were able to detect 1 ng or 460,000 copies of genomic DNA template.

DISCUSSION

The pairwise nucleotide sequence comparison of the PCR GlyA fragments of the two strains of *A. butzleri* and *C. upsaliensis* indicates a nucleotide identities exceeding 97%, thus suggesting a high conservation of nucleotides among different strains of these two species. The nucleotide sequences of the two *A. butzleri*-like strains (# 13217 and # 13218) showed a nucleotide identity of 94.23%. The nucleotide sequences of the two *H. canis* strains (#16953 and #16485) sequenced show identity below 89%. The glyA sequence of *A. butzleri* and *A. butzleri*-like shows high homologues identities in the range of 85.5% to 86.98%. This high degree of nucleotide identity would contribute to the weak cross hybridization observed in the southern blots. The percentage of identity of the GlyA PCR fragment of *C. upsaliensis* and *H. canis* with that of other species was all below 70%, which contributed to the specificity and enhanced the species-specific hybridization of the oligo probes.

The detection of the *Arcobacter butzleri* strain #11556 by with both the *A. butzleri* and *C. upsaliensis* probes suggest that this *A. butzleri* strain is a variant. A partial sequencing of the GlyA PCR fragment indicated a 72.02% nucleotide identity with *A. butzleri* type strain and a 73.21% identity with *C. upsaliensis* type strain. *A. butzleri* reference #11556 is the only strain of *A. butzleri* originated from a water source in Thailand. The rest of the *A. butzleri* strains originated from human or animals in North America or Europe.

Although the 2 oligo probes for *A. butzleri*-like are unable to detect all the strains, a combination of the two probes would be able to detect 9 out of the 10 strains, FIG. 8. The inability of the probe to hybridize to all the strains would suggest a high degree of herterogenecity among the *A. butzleri*-like organisms.

While the present invention has been described with reference to what are presently considered to be the preferred examples, it is to be understood that the invention is not limited to the disclosed examples. To the contrary, the invention is intended to cover various modifications and equivalent arrangements all of which are included within the spirit and scope of the appended claims.

All publications, patents and patent applications herein are incorporated into the present specification by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

Ausubel, F. M., Brent, R., Kingston, R. E., Moore, D. D., Seidman, J. G., Smith, J. A., and Struhl, K. 1990. Current Protocols in Molecular Biology. Greene Publishing Associates and Wiley-Interscience.

Angelaccio, S., Pascarella, S., Fattori, E., Bossa, F., Strong, W., and Schirch, V. 1992. Serine Hydroxymethyltransferase: Origin of Substrate Specificity. Biochemistry. 31:155–162.

Butzler, J. P. (ed.). 1984. Campylobacter: Infection in Man and Animals.

Chan, V. L. and Bingham, H. 1990. Complete Sequence of the *Campylobacter jejuni* glyA gene Encoding Serine Hydroxymethyltransferase. Gene. 101:51–58.

Costas, M., Owen, R. J., and Jackman, P. J. M. 1987. Classification of *Campylobacter sputorum* and Allied Campylobacters based on Numerical Analysis of Electrophoretic Protein Patterns. Syst. Appl. Microbiol. 9:125–131.

Elharrif, Z. and Megraud, F. 1986. Characterization of Thermophilic Campylobacter. II. Enzymatic Profiles. Curr. Microbiol. 13:317–322.

Eyers, M., Chapelle, S., Camp, G. van, Goossens, H., and Wachter, R. de. 1993. Discrimination Among Thermophilic Campylobacter Species by Polymerase Chain Reaction Amplification of 23S rRNA Gene Fragments. J. Clin. Microbiol. 31:3340–3343.

Giesendorf, B. A. J., Belkum, A. van, Koeken, A., Stegeman, H., Henkens, M. H. C., Plas, J. van der, Goossens, H., Niesters, H. G. M., and Quint, W. E. V. 1993. Development of Species-Specific DNA Probes for *Campylobacter jejuni, Campylobacter coli,* and *Campylobacter lari* by Polymerase Chain Reaction Fingerprinting. J. Clin. Microbiol. 31:1541–1546.

Giesendorf, B. A. J., Goossens, H., Niesters, H. G. M., Belkum, A. van, Koeken, A., Endtz, H. P., Stegeman, H., and Quint, W. G. V. 1994. PCR-Mediated DNA Fingerprinting for Epidemiological Studies on Campylobacter spp. J. Med. Microbiol. 40:141–147.

Goodwin, C. S., McCulloch, R. K., Armstrong, J. A., and Wee, S. H. 1985. Unusual Cellular Fatty Acids and Distinctive Ultrastructure in a New Spiral Bacterium (*Campylobacter pyloridis*) from the Human Gastric Mucosa. J. Med. Microbiol. 19:257–267.

Hebert, G. A., Hollis, D. G., Weaver, R. E., Steigerwalt, A. G., McKinney, R. M., and Brenner, D. J. 1983. Serogroups of *Campylobacter jejuni, Campylobacter coli,* and *Campylobacter fetus* Defined by Direct Immunofluorescence. J. Clin. Microbiol. 17:529–538.

Higgins, D. G., Bleasby, A. J., and Suchs, R. 1992. CLUSTAL V: Improved Software for Multiple Sequence Alignment. CABIOS. 8:189–191.

Higgins, D. G. and Sharp, P. M. 1989. Fast and Sensitive Multiple Sequence Alignments on a Microcomputer. CABIOS. 5:151–153.

Innis, M. A., Gelfand, D. H., Sninsky, J. J., and White, T. J. (eds.). 1990. PCR Protocols: A Guide to Methods and Applications. Academic Press, Inc.

Landegren, U., Kaiser, R., Caskey, C. T., and Hood, L. 1988. DNA Diagnostics: Molecular Techniques and Automation. Science. 242:229–237.

Li, C., Ferguson, D. A Jr., Ha, T., Chi, D. S., and Thomas, E. 1993. A Highly Specific and Sensitive DNA Probe Derived from Chromosomal DNA of *Helicobacter pylori* Is Useful for Typing *H. pylori* Isolates. J. Clin. Microbiol. 31:2157–2162.

Macario, A. J. L. and Macario, E. C. de. (eds.). 1990. Gene Probes for Bacteria. Academic Press, Inc.

Megraud, F., Bonnet, F., Garnier, M., and Lamouliatte, H. 1985. Characterization of "*Campylobacter pyloridis*" by Culture, Enzymatic Profile and Protein Content. J. Clin. Microbiol. 22:1007–1010.

Paster, B. J., and Dewhirst, F. E. 1988. Phylogeny of Campylobacters, Wolinellas, *Bacteroides gracilis,* and *Bacteroides ureolyticus* by 16S Ribosomal Ribonucleic Acid Sequencing. Int. J. Syst. Bacteriol. 38:56–62.

Paster, B. J., Lee, A., Fox, J. G., Dewhirst, F. E., Tordoff, L. A., Fraser, G. J., O'Rourke, J. L., Taylor, N. S., and Ferrero, R. 1991. Phylogeny of *Helicobacter felis* sp. nov., *Helicobacter mustelae*, and Related Bacteria. Int. J. Syst. Bacteriol. 41:31–38.

Patton, C. M., Wachsmuth, I. K., Evins, G. M., Kiehlbauch, J. A., Plikaytis, B. D., Troup, N., Tompkins, L., and Lior, H. 1991. Evaluation of 10 Methods To Distinguish Epidemic-Associated Campylobacter Strains. J. Clin. Microbiol. 29:680–688.

Penner, J. L. 1988. The Genus Campylobacter: a Decade of Progress. Clin. Microbiol. Rev. 1:157–172.

Plamann, M., Stauffer, L. T., Urbanowski, M. L., and Stauffer, G. V. 1983. Complete Nucleotide Sequence of the *E. coli* glyA gene. Nucleic Acids Res. 11:2065–2075.

Sambrook, J., Fritsch, E. F., Maniatis, T. 1989. Molecular Cloning: A Laboratory Manual, Second Edition. Cold Spring Harbor Laboratory Press. Sanger, F., Nicklen, S., and Coulson, A. R. 1977. DNA Sequencing with Chain-Terminating Inhibitors. Proc. Natl. Acad. Sci. USA. 74:5463–5467.

Schirch, V., Hopkins, S., Villar, E., and Angelaccio, S. 1985. Serine Hydroxymethyltransferase from *Escherichia coli*: Purification and Properties. J. Bacteriol. 163:1–7.

Thompson, L. M., Smibert, R. M., Johnson, J. L., and Krieg, N. R. 1988. Phylogenetic Study of the Genus Campylobacter. Int. J. Syst. Bacteriol. 38:190–200.

Totten, P. A., Patton, C. M., Tenover, F. C., Barrett, T. J., Stamm, W. E., Steigerwalt, A. G., Lin, J. Y., Holmes, K. K., and Brenner, D. J. 1987. Prevalence and Characterization of Hippurate-Negative *Campylobacter jejuni* in King County, Washington. J. Clin. Microbiol. 25:1747–1752.

Vandamme, P., and De Ley, J. 1991. Proposal for a New Family, Campylobacteraceae. Int. J. Syst. Bacteriol. 41:451–455.

Vandamme, P., Falsen, E., Rossau, R., Hoste, B., Segers, P., Tytgat, R., and De Ley, J. 1991. Revision of Campylobacter, Helicobacter, and Wolinella Taxonomy: Emendation of Generic Descriptions and Proposal of Arcobacter gen. nov. Int. J. Syst. Bacteriol. 41:88–103.

Vandamme, P., Giesendorf, B. A. J., Belkum, A. van, Pierard, D., Lauwers, S., Kersters, K., Butzler, J. -P., Goossens, H., and Quint, W. G. V. 1993. Discrimination of Epidemic and Sporadic Isolates of *Arcobacter butzleri* by Polymerase Chain Reaction-Mediated DNA Fingerprinting. J. Clin. Microbiol. 31:3317–3319.

Vandamme, P., Vancanneyt, M., Pot, B., Mels, L., Hoste, B., Dewettinck, D., Vlaes, L., Van Den Borre, C., Higgins, R., Hommez, J., Kersters, K., Butzler, J. -P., and Goossens, H. 1992. Polyphasic Taxonomic Study of the Emended Genus Arcobacter with *Arcobacter butzleri* comb. nov. and *Arcobacter skirrowii* sp. nov., an Aerotolerant Bacterium Isolated from Veterinary Specimens. Int. J. Syst. Bacteriol. 42:344–356.

Ursing, J. B., Lior, H., and Owen, R. J. 1994. Proposal of Minimal Standards for Describing New Species of the Family Campylobacteraceae. Int. J. Syst. Bacteriol. 44:842–845.

Wetherall, B. L. and Johnson, A. M. 1990. Nucleic Acid Probes for Campylobacter Species, pp. 255–293. In A. J. L. Macario and E. C. de Macario (eds.), Gene Probes for Bacteria—1990. Academic Press, Inc.

Woese, C. R. 1987. Bacterial Evolution. Microbiol. Rev. 51:221–271.

DETAILED FIGURE LEGENDS

FIG. 1. Multiple nucleotide sequence alignment of the partial glyA sequences. Alignment of the sequences from *C. jejuni* ATCC 33560, *C. coli* ATCC 33559, *C. lari* ATCC 35221, *C. upsaliensis* ATCC 43954, *H. cinaedi* ATCC 35683, *H. pylori* (clinical isolate), and *A. nitrofigilis* ATCC 33309. The boxed regions were used to design and synthesize the species-specific oligo probes.

FIG. 2. PCR products of all species resolved in a 1% agarose gel and used in the Southern hybridization experiments.

The molecular weight markers are in lanes L (HindIII-digested lambda phage DNA), and M (100 bp ladder). The PCR products of each bacterial strain are in the following lanes: lanes 1 to 13 are *C. jejuni* strains ATCC 33560, ATCC 43429, ATCC 43430, ATCC 43431, ATCC 43432, ATCC 43433, CEPA-3C, COO6-85, INN7383, V48, D594, D603, and D1916; lanes 14, 15 and 16 are *C. coli* ATCC 33559, *C. lari* ATCC 35221, and *C. lari* PC 637, respectively; lanes 17 to 26 are *C. coli* strains ATCC 33559, LMG 7535, LMG 8530, LMG 9853, LMG 9854, LMG 9855, LMG 9856, LMG 9857, LMG 9858, and LMG 9859; lanes 27 to 40 are *C. lari* strains ATCC 35221, LMG 8845, LMG 8844, LMG 7929, LMG 9887, LMG 9888, LMG 9889, LMG 9913, LMG 9914, LMG 9152, LMG 9253, LMG 11251, 2314 RG, and 2665 BVA; lanes 41 to 54 are *C. upsaliensis* strains ATCC 43954, 12030, 13064, 13950, 14013, 14080, 14506, 14510, 14526, 14529, 14530, 14532, 14967, and 15172; lane 55 to 61 are *C. sputorum* subsp. bubulus ATCC 33562, *H. cinaedi* ATCC 35683, *H. pylori* (clinical isolate), *A. nitrofigilis* ATCC 33309, *E. coli* ATCC 9637, *P. aeruginosa* ATCC 10145, and *S. sonnei* ATCC 11803, respectively; and finally, lanes 62 to 68 are the glyA recombinant plasmids of *C. jejuni* ATCC 33560, *C. coli* ATCC 33559, *C. lari* ATCC 35221, *C. upsaliensis* ATCC 43954, *H.cinaedi* ATCC 35683, *H. pylori* (clinical isolate), and *A. nitrofigilis* ATCC 33309, respectively. Lane designations are maintained for all figures.

FIG. 3. Autoradiographs of the Southern hybridizations testing the species-specificity of the series 1 probes. Unless noted, no cross-hybridizations were observed on the autoradiographs taken after 20 hours of exposure.

Panel (A). CJATC-1 probe hybridizing to *C. jejuni* strains. Autoradiograph after 4 hours of exposure. After 21 hours of exposure, cross- hybridization to *C. coli* was observed.

Panel (B). CC-1 probe hybridizing to *C. coli* strains. Autoradiograph taken after 2 hours of exposure.

Panel (C). CL-1 probe hybridizing to *C. lari* strains. Autoradiograph taken after 2 hours of exposure. After 20 hours of exposure, cross-hybridization to *A. nitrofigilis* was observed.

Panel (D). CU-1 probe hybridizing to *C. upsaliensis* strains. Autoradiograph taken after 4 hours of exposure.

Panel (E). HC-1 probe hybridizing to *H. cinaedi* ATCC 35683. Autoradiograph taken after 4 hours of exposure.

Panel (F). HP-1 probe hybridizing to *H. pylori* (clinical isolate). Autoradiograph taken after 4 hours of exposure.

Panel (G). AN-1 probe hybridizing to *A. nitrofigilis* ATCC 33309. Autoradiograph taken after 40 minutes of exposure.

FIG. 4. Autoradiographs of the Southern hybridizations testing the species-specificity of the series 2 probes. All autoradiographs were taken after 22 hours of exposure.

Panel (A). CJATC-2 probe hybridizing to *C. jejuni* strains. Cross-hybridization to *C. upsaliensis* was observed.

Panel (B). CC-2 probe hybridizing to *C. coli* strains. No cross-hybridization was observed.

Panel (C). CL-2 probe hybridizing to *C. lari* strains. Cross-hybridization to *C. upsaliensis* was observed.

Panel (D). CU-2 probe hybridizing to *C. upsaliensis* strains. Cross-hybridization to *C. jejuni* was observed.

FIG. 5. Sensitivity of the PCR/hybridization strategy.

Panel (A). PCR products resulting from the various amounts (in ug) of template *C. jejuni* ATCC 33560 genomic DNA used. Lanes a to g are: $1\times10^{-5}$ ug, $8\times10^{-6}$ ug, $6\times10^{-6}$ ug, $4\times10^{-6}$ ug, $2\times10^{-6}$ ug, $1\times10^{-6}$ ug, and no DNA.

Panel (B). Autoradiograph of the southern hybridization using the CJATC-1 probe which is detecting 10 ul of the 100 ul PCR using $4\times10^{-6}$ ug ($4\times10^{-12}$ grams) template DNA.

FIG. 6: The multiple sequence alignment using ClustalW alignment program. The following abbreviations are used: CU—*C. upsaliensis*, AB—*A. butzleri*, BL—*A. butzleri*-like, and HC—*H. canis*. The stars below the sequences represent conserved bases. The locations of the species-specific oligo probes are boxed.

Figure 7:
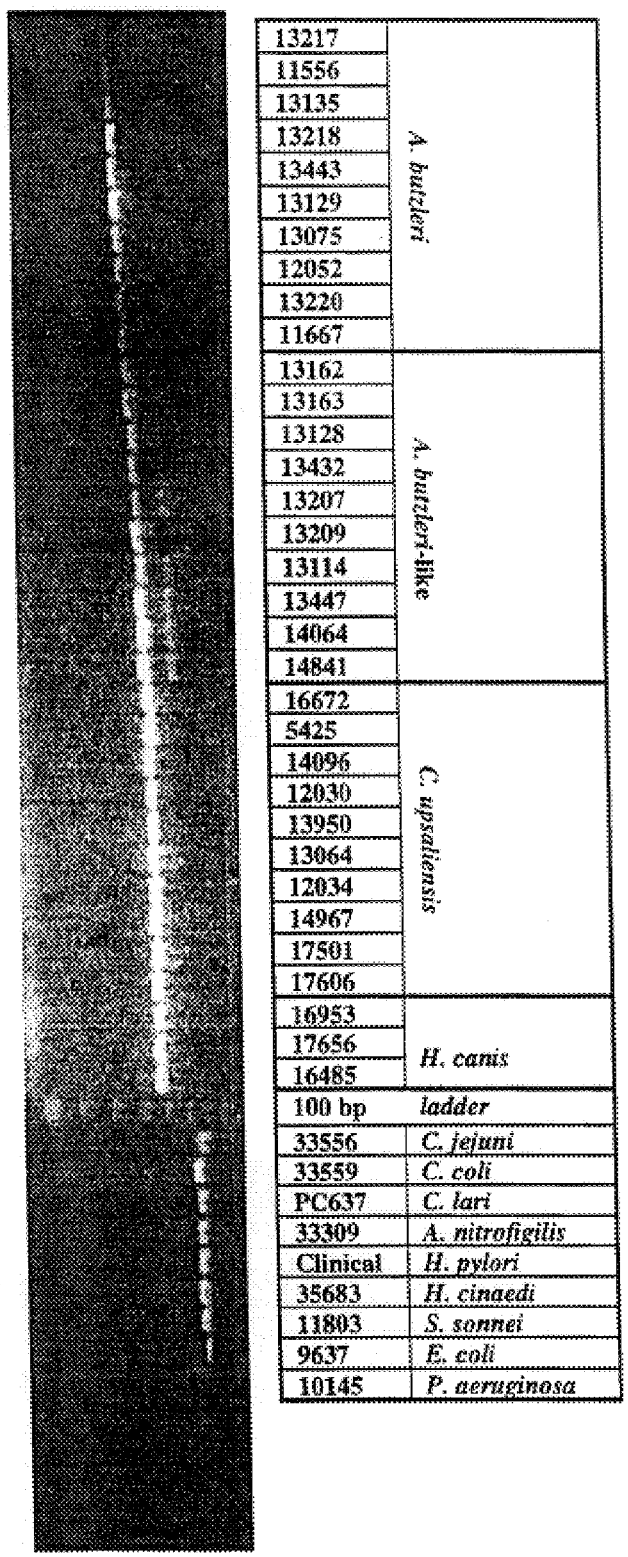
FIG. 7 shows the PCR products of A. butzleri, A. butzleri-like, C. upsaliensis, and H. canis.

FIG. 7: The PCR products of *A. butzleri*, *A. butzleri*-like, *C. upsaliensis*, and *H. canis* using S1–S5 primers and the PCR products of the other species using S1–S2 primers are ran on 1.5% agarose gel and blotted onto Hybond membrane. The reference number of each strains are as indicated, along with the 100 bp ladder.

FIG. 8: The hybridization results with each of the species-specific oligo probes. Panel A indicated exposure time of 4 hours and panel B represented overnight exposure. The stringency of the washing condition is 0.2X SSC+0.1% SDS with increasing temperatures. The temperatures along with the oligo probe used are indicated on the left. The relevant hybridizing fragments of the corresponding species are also indicated above each blot.

TABLE 1

Reference bacteria used in Example 1.

| Bacteria | Strain[o] | Bacteria | Strain[o] |
|---|---|---|---|
| *Esherichia coli* | JM101[1] | *Campylobacter lari* | ATCC 35221 (type) [*+] |
|  | ATCC 9637[+] |  | PC 637[4+] |
|  |  |  | LMG 8845[6+] |
| *Campylobacter jejuni* | ATCC 33560 (type)[*+#] |  | LMG 8844[6+] |
|  | ATCC 43429[*] |  | LMG 7929[6+] |
|  | ATCC 43430[*] |  | LMG 9887[6+] |
|  | ATCC 43431[*] |  | LMG 9888[6+] |
|  | ATCC 43432[*] |  | LMG 9889[6+] |
|  | ATCC 43433[*] |  | LMG 9913[6+] |
|  | CEPA3C[2+] |  | LMG 9914[6+] |
|  | COO6-85[2+] |  | LMG 9152[6+] |
|  | INN7383[2+] |  | LMG 9253[6+] |
|  | V48[2+] |  | LMG 11251[6+] |
|  | D594[3+] |  | 2314 RG[6+] |
|  | D603[3+] |  | 2665 BVA[6+] |
|  | D1916[3+] |  |  |
| *Campylobacter coli* | ATCC 33559 (type)[*+] | *Campylobacter upsaliensis* | ATCC 43954 (type)[*+] |
|  | LMG 7535[6+] |  | 12030 |
|  | LMG 8530[6+] |  | 13064 |
|  | LMG 9853[6+] |  | 13950 |

TABLE 1-continued

Reference bacteria used in Example 1.

| Bacteria | Strain[0] | Bacteria | Strain[0] |
|---|---|---|---|
| | LMG 9854[6+] | | 14013 |
| | LMG 9855[6+] | | 14080 |
| | LMG 9856[6+] | | 14506 |
| | LMG 9857[6+] | | 14510 |
| | LMG 9858[6+] | | 14526 |
| | LMG 9859[6+] | | 14529 |
| | LMG 15882[6+] | | 14530 |
| | | | 14532 |
| | | | 14967 |
| | | | 15172 |
| | | Campylobacter sputorum subsp. bubulus | ATCC 33562 (type)*+ |
| | | Helicobacter cinaedi | ATCC 35683 (type)*+ |
| | | Helicobacter pylori | Clinical isolate*+ |
| | | Arcobacter nitrofigilis | ATCC 33309 (type)*+ |
| | | Bifidobacterium adolescentis | ATCC 15703**+ |
| | | Lactobacillus casei | 5+ |
| | | Pseudomonas aeruginosa | ATCC 10145* |
| | | Shigella sonnei | ATCC 11803* |

[0]ATCC, American Type Culture Collection, Rockville, U.S.A.
[1]supE thi Δ(lac-proAB)
F'[traD36 proAB+ lacI[q] lacZΔM15] (Schirch et al., 1985)
[2]Clinical isolates
[3]Hippuricase negative variants (Vandamme et al., 1992)
[4]Obtained from Dr. J. L. Penner, University of Toronto, Toronto, Ontario, Canada
[5]Obtained from Dr. A. Bognar, University of Toronto, Toronto, Ontario, Canada
[6]Obtained from Dr. P. Vandamme, Laboratorium voor Microbiologie, Belgium
*strains used for the PCR, subcloned, and sequenced to generate the species-specific oligo probes
+strains used for the PCR and Southern hybridizations to determine species-specificity of the probes
C. jejuni type strain used to determine sensitivity of this PCR/hybridization strategy

TABLE 2

Summary of the Southern hybridization results of probe specificity. And the use of seven probes in each diagnostic set 1 or 2 to detect and differentiate the different Campylobacter spp., Helicobacter spp., and A. nitrofigilis. N/A - not applicable.

| Probes: | Detects: | Diagnostic Set: |
|---|---|---|
| CJATC-1 | C. jejuni/C. coli | 1 |
| CC-1 | C. coli | 1 |
| CL-1 | C. lari/A. nitrofigilis | 1 |
| AN-1 | A. nitrofigilis | 1,2 |
| HC-1 | H. cinaedi | 1,2 |
| HP-1 | H. pylori | 1,2 |
| CU-1 | C. upsaliensis | 1,2 |
| CJATC-2 | C. jejuni/C. upsaliensis | 2 |
| CL-2 | C. lari/C. upsaliensis | 2 |
| CC-2 | C. coli | 2 |
| CU-2 | C. upsaliensis/C. jejuni | N/A |

TABLE 3

Bacterial strains used in Example 2

| Bacteria | Strain | Bacteria | Strain |
|---|---|---|---|
| Arcobacter butzleri | Reference #13217 or ATCC 49616 | Arcobacter butzleri-like | Reference #13162 |
| | Reference #11556 | | Reference #13163 |
| | Reference #13135 | | Reference #13128 |
| | Reference #13218 | | Reference #13432 |
| | Reference #13443 | | Reference #13207 |
| | Reference #13129 | | Reference #13209 |
| | Reference #13075 | | Reference #13114 |
| | Reference #12052 | | Reference #13447 |
| | Reference #13220 | | Reference #14064 |
| | Reference #11667 | | Reference #14841 |
| Campylobacter upsaliensis | Reference #16672 or ATCC 43954 | Helicobacter canis | Reference #16953 or ATCC 51401 |
| | Reference #5424 | | Reference #17656 |
| | Reference #14096 | | Reference #16485 |
| | Reference #12030 | | |
| | Reference #13950 | | |
| | Reference #13064 | | |
| | Reference #12034 | | |
| | Reference #14967 | | |
| | Reference #17501 | | |
| | Reference #17606 | | |
| Campylobacter jejuni | ATCC 33556 | Shigella sonnei | ATCC 11803 |
| Campylobacter coli | ATCC 33559 | Escherichia coli | ATCC 9637 |
| Campylobacter lari | PC637 | Pseudomonas aeruginosa | ATCC 10145 |
| Arcobacter nitrofigilis | ATCC 33309 | | |
| Helicobacter pylori | Clinical Isolate | | |
| Helicobacter cinaedi | ATCC 35683 | | |

TABLE 4

The percentages of nucleotide identity by pairwise
comparison of partial glyA sequences
AB - *Arcobacter butzleri*
BL - *Arcobacter butzleri*-like
CU - *Campylobacter upsaliensis*
HC - *Helicobacter canis*

| Strains | AB #13217 | AB #13218 | BL #13432 | BL #13207 | CU #16672 | CU #14096 | HC #16953 | HC #16485 |
|---|---|---|---|---|---|---|---|---|
| AB #13217 | 100% | 98.32% | 86.43% | 85.50% | 68.40% | 67.65% | 61.33% | 61.71% |
| AB #13218 |  | 100% | 86.98% | 86.61% | 68.02% | 67.10% | 61.33% | 62.08% |
| BL #13432 |  |  | 100% | 94.23% | 69.70% | 68.58% | 61.71% | 62.08% |
| BL #13207 |  |  |  | 100% | 69.14% | 68.48% | 61.15% | 60.96% |
| CU #16672 |  |  |  |  | 100% | 97.03% | 65.30% | 64.56% |
| CU #14096 |  |  |  |  |  | 100% | 65.30% | 64.56% |
| HC #16953 |  |  |  |  |  |  | 100% | 88.52% |
| HC #16485 |  |  |  |  |  |  |  | 100% |

TABLE 5

The sequences and melting temperature of the species-specific oligo probes

| NAME | SEQUENCE | Tm |
|---|---|---|
| GlyA-AB | 5'-GCT TCT GCA TAC GCA AGA GAA ATT GAT TCA AA-3' | 64.36 |
| GlyA-BL | 5'-GCA AGT GCA TAT GCA AGA GAG ATT GAT TTT AA-3' | 63.27 |
| GlyA-BL2 | 5'-AAG TAA ACC AAG CTT TTC AGG GCA AAA CTA CTC T-3' | 65.58 |
| GlyA-CU | 5'-GGT TAG TAG CTC GGG TAA AAT GTA TGA AAG C-3' | 65.52 |
| GlyA-HC | 5'-CAG GAT TGA TTA CGA CAA GCT ACG CCA AAG CGC GC-3' | 71.24 |
| GlyA-HC2 | 5'-TTC TGC CTA TAC AAG AGA GCT AGA TTT TGC CAA G-3' | 67.12 |

We claim:

1. An isolated nucleic acid probe comprising at most 34 nucleotides and selected from the group consisting of: (a) a nucleic acid probe having a sequence of SEQ ID NO: 1; (b) a nucleic acid probe having the sequence of SEQ ID NO: 2; (c) a nucleic acid probe having a sequence of SEQ ID NO: 3; (d) a nucleic acid probe having a sequence of SEQ ID NO: 4; (e) a nucleic acid probe having a sequence of SEQ ID NO: 5; (f) a nucleic acid probe having a sequence of SEQ ID NO: 6; (g) a nucleic acid probe having a sequence of SEQ ID NO: 7; (h) a nucleic acid probe having a sequence of SEQ ID NO: 8; (i) a nucleic acid probe having a sequence of SEQ ID NO: 9; (j) a nucleic acid probe having a sequence of SEQ ID NO: 10; (k) a nucleic acid probe having a sequence of SEQ ID NO: 11; (l) a nucleic acid probe having a sequence of SEQ ID NO: 12; (m) a nucleic acid probe having a sequence of SEQ ID NO: 13; (n) a nucleic acid probe having a sequence of SEQ ID NO: 14; (o) a nucleic acid probe having a sequence of SEQ ID NO: 15; (p) a nucleic acid probe having a sequence of SEQ ID NO: 16; (q) a nucleic acid probe having a sequence of SEQ ID NO: 17; and (r) a nucleic acid sequence that is fully complementary to (a) or (b) or (c) or (d) or (e) or (f) or (g) or (h) or (i) or (j) or (k) or (l) or (m) or (n) or (p) or (q).

2. An isolated nucleic acid probe for detecting or identifying C. jejuni which consists of SEQ ID NO: 1, SEQ ID NO: 2, or a nucleic acid sequence fully complementary thereto.

3. An isolated nucleic acid probe for detecting or identifying C. coli which consists of SEQ ID NO: 3, SEQ ID NO: 4, or a nucleic acid sequence fully complementary thereto.

4. An isolated nucleic acid probe for detecting or identifying C. lari which consists of SEQ ID NO: 5, SEQ ID NO: 6, or a nucleic acid sequence fully complementary thereto.

5. An isolated nucleic acid probe for detecting or identifying C. upsaliens which consists of SEQ ID NO: 7, SEQ ID NO: 8, SEQ ID NO: 15 or a nucleic acid sequence fully complementary thereto.

6. An isolated nucleic acid probe for detecting or identifying H. cinaedi which consists of SEQ ID NO: 9, or a nucleic acid sequence fully complementary thereto.

7. An isolated nucleic acid probe for detecting or identifying H. pylori which consists of SEQ ID NO: 10, or a nucleic acid sequence fully complementary thereto.

8. An isolated nucleic acid probe for detecting or identifying A. nitrofigalis which consists of SEQ ID NO: 11, or a nucleic add sequence fully complementary thereto.

9. An isolated nucleic acid probe for detecting or identifying A. butzleri which consists of SEQ ID NO: 12, or a nucleic acid sequence fully complementary thereto.

10. An isolated nucleic acid probe for detecting or identifying A. butzleri-like bacterium which consists of SEQ ID NO: 13, SEQ ID NO: 14, or a nucleic acid sequence fully complementary thereto.

11. An isolated nucleic acid probe for detecting or identifying H. canis which consists of SEQ ID NO: 16, SEQ ID NO: 17, or a nucleic acid sequence fully complementary thereto.

12. A method for detecting the presence of a Campylobacter, Helicobacter or Arcobacter spp. bacteria in a sample comprising:

(a) contacting the nucleic acid molecules of the sample, under hybridization conditions, with one or more of nucleic add probes:

CJATC-1 SEQ ID NO: 1;
CJATC-2 SEQ ID NO: 2;
CC-1 SEQ ID NO: 3;
CC-2 SEQ ID NO: 4;
CL-1 SEQ ID NO: 5;
CL-2 SEQ ID NO: 6;
CU-1 SEQ ID NO: 7;
CU-2 SEQ ID NO: 8;
HC-1 SEQ ID NO: 9;
HP-1 SEQ ID NO: 10;
AN-1 SEQ ID NO: 11;
GlyA-AB SEQ ID NO 12;
GlyA-BL SEQ ID NO 13;
GlyA-BL2 SEQ ID NO 14;
GlyA-CU SEQ ID NO 15;
GlyA-HC SEQ ID NO 16;
GlyA-HC2 SEQ ID NO 17;

or nucleic acid sequences fully complementary thereto and (b) determining if the nucleic acid molecules in the sample sample hybridizes with the nucleic acid probe (s) thereby detecting any Campylobacter, Helicobacter or Arcobacter bacteria in said sample.

13. A method for identifying any one of Campylobacter jejuni (C. Jejuni), Campylobacter coli (C. coli), Campylobacter lari (C. lari) and Campylobacter upsaliens (C. upsaliens); Helicobacter cinaedi (H. cinaedi), Helicobacter

*pylori* (*H. pylori*), *Helicobacter canis*(*H. canis*), *Arcobacter nitrofigalis* (*A. nitrofigalis*) *Arcobacter butzleri* (*A. butzleri*); and *Arcobacter butzlerii*-like(*A. butzlerii*-like) bacterium in a sample, the method comprising the method of claim 12, and the further step of correlating the nucleic acid probe(s) which hybridize with the identity of the bacteria.

14. A kit for detecting the presence of a Campylobacter, Helicobacter or Arcobacter bacteria in a sample comprising: (a) one or more of nucleic acid probes:

CJATC-1 SEQ ID NO: 1;
CJATC-2 SEQ ID NO: 2;
CC-1 SEQ ID NO: 3;
CC-2 SEQ ID NO: 4;
CL-1 SEQ ID NO: 5;
CL-2 SEQ ID NO: 6;
CU-1 SEQ ID NO: 7;
CU-2 SEQ ID NO: 8;
HC-1 SEQ ID NO: 9;
HP-1 SEQ ID NO:10;
AN-1 SEQ ID NO: 11;
GlyA-AB SEQ ID NO 12;
GlyA-BL SEQ ID NO 13;
GlyA-BL2 SEQ ID NO 14;
GlyA-CU SEQ ID NO 15;
GlyA-HC SEQ ID NO 16;
GlyA-HC2 SEQ ID NO: 17;

or nucleic acid sequences fully complementary thereto; (b) reagents required for hybridization of the nucleic acid probe with the nucleic acid molecules in the sample; and (c) directions for its use.

15. The kit of claim 14 for identifying any one of *Campylobacter jejuni* (*C. Jejuni*), *Campylobacter coli* (*C. coli*), *Campylobacter lari* (*C. lari*) and *Campylobacter upsaliens* (*C. upsaliens*); *Helicobacter cinaedi* (*H. cinaedi*), *Helicobacter pylori* (*H. pylori*), *Helicobacter canis*(*H. canis*), *Arcobacter nitrofigalis* (*A. nitrofigalis*) *Arcobacter butzleri* (*A. butzleri*); or *Arcobacter butzlerii*-like(*A. butzlerii*-like).

16. A method for detecting *C.jejuni* in a sample by detecting (a) nucleic acid molecule in the sample comprising: contacting the nucleic acid molecules of the sample, under hybridization conditions, with one or both of the nucleic acid probes CJATC-1 (SEQ ID NO: 1) or CJATC-2 (SEQ ID NO: 2), or a nucleic acid sequence fully complementary thereto, and (b) determining if the nucleic acid molecules in the samples hybridize with the nucleic acid probe(s), thereby detecting any *C. jejuni* in said sample.

17. A method for detecting *C.coli* in a sample by detecting a nucleic acid molecule in the sample comprising: contacting the nucleic acid molecules in the sample, under hybridization conditions, with one or both of the nucleic acid probe CC-1 (SEQ ID NO: 3) or CC-2 (SEQ ID NO: 4), or a nucleic acid sequence fully complementary thereto, and (b) determining if the nucleic acid molecules in the samples hybridize with the nucleic acid probe(s), thereby detecting any *C.coli* in said sample.

18. A method for detecting *C.lari* in a sample by detecting a nucleic acid molecule in the sample comprising: contacting the nucleic acid molecules in the sample, under hybridization conditions, with one or both of the nucleic acid probe CL-1 (SEQ ID NO: 5) or CL-2 (SEQ ID NO: 6), or a nucleic acid sequence fully complementary thereto, and (b) determining if the nucleic acid molecules in the samples hybridize with the nucleic acid probe(s), thereby detecting any *C.lari* in said sample.

19. A method for detecting *C.upsaliens* in a sample by detecting a nucleic acid molecule in the sample comprising: contacting the nucleic acid molecules in a sample, under hybridization conditions, with one or more of the nucleic acid probes CU-1 (SEQ ID NO: 7) or CU-2 (SEQ ID NO: 8), or GlyA-CU (SEQ ID NO: 15) or a nucleic acid sequence fully complementary thereto, and (b) determining if the nucleic acid molecules in the samples hybridize with the nucleic acid probe(s), thereby detecting any *C.upsaliens* in said sample.

20. A method for detecting *H.cinaedi* in a sample by detecting a nucleic acid molecule in the sample comprising: contacting the nucleic acid molecules in a sample, under hybridization conditions, with the nucleic acid probe HC-1 (SEQ ID NO: 9), or a nucleic acid sequence fully complementary thereto, and (b) determining if the nucleic acid molecules in the samples hybridize with the nucleic acid probe(s), thereby detecting any *H.cinaedi* in said sample.

21. A method for detecting *H.pylori* in a sample by detecting a nucleic acid molecule in the sample comprising: contacting the nucleic acid molecules in a sample, under hybridization conditions, with the nucleic acid probe HP-1 (SEQ ID NO: 10), or a nucleic acid sequence fully complementary thereto, and (b) determining if the nucleic acid molecules in the samples hybridize with the nucleic acid probe(s), thereby detecting any *H.pylori* in said sample.

22. A method for detecting *H. canis* in a sample by detecting a nucleic acid molecule in the sample comprising: contacting the nucleic acid molecules in a sample, under hybridization conditions, with the nucleic acid probe GlyA-HC (SEQ ID NO: 16), or GlyA-HC2 (SEQ ID NO: 17), or a nucleic acid sequence fully complementary thereto, and (b) determining if the nucleic acid molecules in the samples hybridize with the nucleic acid probe(s), thereby detecting any *H. canis* in said sample.

23. A method for detecting *A.nitrofigilis* in a sample by detecting a nucleic acid molecule in the sample comprising: contacting the nucleic acid molecules in a sample, under hybridization conditions, with the nucleic acid probe AN-1 (SEQ ID NO: 11), or a nucleic acid sequence fully complementary thereto, and (b) determining if the nucleic acid molecules in the samples hybridize with the nucleic acid probe(s), thereby detecting any *A.nitrofigilis* in said sample.

24. A method for detecting *A. butzleri* in a sample by detecting a nucleic acid molecule in the sample comprising: contacting the nucleic acid molecules in a sample, under hybridization conditions, with the nucleic acid probe GlyA-AB (SEQ ID NO: 12), or a nucleic acid sequence fully complementary thereto, and (b) determining if the nucleic acid molecules in the samples hybridize with the nucleic acid probe(s), thereby detecting any *A. butzleri* in said sample.

25. A method for detecting *A. butzleri*- like bacterium in a sample by detecting a nucleic acid molecule in the sample comprising: contacting the nucleic acid molecules in a sample, under hybridization conditions, with the nucleic acid probe GlyA-BL (SEQ ID NO. 13), or GlyA-BL2 (SEQ ID NO: 14), or a nucleic acid sequence fully complementary thereto, and (b) determining if the nucleic acid molecules in the samples hybridize with the nucleic acid probe(s), thereby detecting any said bacterium in said sample.

* * * * *

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: other nucleic acid (xi) SEQUENCE DESCRIPTION: SEQ ID NO: 1:

TTTTCCGCAC ACTCATGTAG TAAGCTCAAC TA                        32

(2) INFORMATION FOR SEQ ID NO: 2:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: other nucleic acid (xi) SEQUENCE DESCRIPTION: SEQ ID NO: 2:

GAAAAAGTAA GAGAAATTGC TAAAAAAGAA                           30

(2) INFORMATION FOR SEQ ID NO: 3:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: other nucleic acid (xi) SEQUENCE DESCRIPTION: SEQ ID NO: 3:

ATTTCCTCAT GCTCATGTAG TAAGCTCTAC AA                        32

(2) INFORMATION FOR SEQ ID NO: 4:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: other nucleic acid (xi) SEQUENCE DESCRIPTION: SEQ ID NO: 4:

GAAAAAGTTA GGGAAATTGC TCATATTGTA                           30

(2) INFORMATION FOR SEQ ID NO: 5:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: other nucleic acid (xi) SEQUENCE DESCRIPTION: SEQ ID NO: 5:

ATTCCCTTAT GCTCATGTTG TAAGTTCT                                              28

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

GATAAAGTTA GAGAGATAGC AAAAGAGATT                                            30

(2) INFORMATION FOR SEQ ID NO: 7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

TTTCCCTCAC GCACACATCG TAAGCTCA                                              28

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

GAAAAAGTAA GAGAAATAGC ACACATCGTT                                            30

(2) INFORMATION FOR SEQ ID NO: 9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 9:

TGAGCGCGTG AAGCAGCTAT TTGGCTGTGC GT                                         32

(2) INFORMATION FOR SEQ ID NO: 10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 10:

AGAAAGGGCT AAAAAGCTTT TCAATTGCCA GT                                         32

(2) INFORMATION FOR SEQ ID NO: 11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

```
AGATAGAGCT TGTGAAATTT TTGGTTGTAA AT                              32
```

(2) INFORMATION FOR SEQ ID NO: 12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

```
GCTTCTGCAT ACGCAAGAGA AATTGATTCA AA                              32
```

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

```
GCAAGTGCAT ATGCAAGAGA GATTGATTTT AA                              32
```

(2) INFORMATION FOR SEQ ID NO: 14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 14:

```
AAGTAAACCA AGCTTTTCAG GGCAAAACTA CTCT                            34
```

(2) INFORMATION FOR SEQ ID NO: 15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 15:

```
GGTTAGTAGC TCGGGTAAAA TGTATGAAAG C                               31
```

(2) INFORMATION FOR SEQ ID NO: 16:

(i) SEQUENCE CHARACTERISTICS:
        (A) LENGTH: 35 base pairs

```
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 16:

CAGGATTGAT TACGACAAGC TACGCCAAAG CGCGC                                    35

(2) INFORMATION FOR SEQ ID NO: 17:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 17:

TTCTGCCTAT ACAAGAGAGC TAGATTTTGC CAAG                                     34
```